US007763765B2

(12) United States Patent
Kuechler et al.

(10) Patent No.: US 7,763,765 B2
(45) Date of Patent: *Jul. 27, 2010

(54) METHOD OF HIGH PRESSURE AND HIGH CAPACITY OXYGENATE CONVERSION WITH CATALYST EXPOSURE CYCLE

(75) Inventors: Keith H. Kuechler, Friendswood, TX (US); James H. Beech, Kingwood, TX (US); Doron Levin, Annandale, NJ (US); Stephen N. Vaughn, Kingwood, TX (US); Stephen H. Brown, Bernardsville, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 764 days.

This patent is subject to a terminal disclaimer.

(21) Appl. No.: 11/698,511

(22) Filed: Jan. 26, 2007

(65) Prior Publication Data
US 2007/0232844 A1 Oct. 4, 2007

Related U.S. Application Data

(60) Provisional application No. 60/788,147, filed on Mar. 31, 2006.

(51) Int. Cl.
*C07C 1/00* (2006.01)

(52) U.S. Cl. ........................ 585/639; 585/326; 585/327; 585/634; 585/640; 585/642; 208/146

(58) Field of Classification Search ................. 208/146; 585/326, 327, 634, 639, 640, 642
See application file for complete search history.

(56) References Cited

U.S. PATENT DOCUMENTS 4,814,541 A  3/1989  Lewis
5,126,308 A  6/1992  Barger et al.
5,811,621 A  9/1998  Van Dijk (Continued)

FOREIGN PATENT DOCUMENTS

WO  WO 01/85872  11/2001

(Continued)

*Primary Examiner*—Glenn Caldarola
*Assistant Examiner*—Prem C. Singh
(74) *Attorney, Agent, or Firm*—Kevin M. Faulkner; David M. Weisberg

(57) ABSTRACT

A gas-solids reaction system is provided for improving product recovery in a multiple reactor reaction system. An oxygenate feedstock, desirably of high concentration in oxygenate, is reacted with a catalyst having a low to modest acidity and a Si/Al$_2$ ratio of from 0.10 to 0.32. The reaction occurs in a reaction zone of a fluidized bed reactor at an oxygenate partial pressure of at least 45 psia and a reactor gas superficial velocity of at least 10 ft/s, conveying catalyst through the reaction zone to a circulation zone. The catalyst undergoes displacement with an inert gas in the circulation zone at a displacement gas superficial velocity of at least 0.03 m/s, after which at least a portion, preferably a large portion is returned to the reaction zone. The catalyst has a residence time in the circulation zone of at least twice that of the residence time of catalyst in the reaction zone. Extraordinary catalyst activity at high olefin selectivity results despite insignificant changes in coke on catalyst and coke yield when compared to lower pressure operations.

21 Claims, 17 Drawing Sheets

U.S. PATENT DOCUMENTS 6,441,261 B1 8/2002 Kuechler et al.
6,531,639 B1 3/2003 Fung et al.
6,613,950 B1 9/2003 Vaughn et al.
6,673,978 B2 1/2004 Coute et al.
6,740,791 B2 * 5/2004 Kuechler et al. ............ 585/639

2004/0104148 A1 6/2004 Lomas et al.

FOREIGN PATENT DOCUMENTS

WO    WO 2005/061418    7/2005

* cited by examiner

Activity of Catalyst A in Reactor/Regenerator A at various conditions

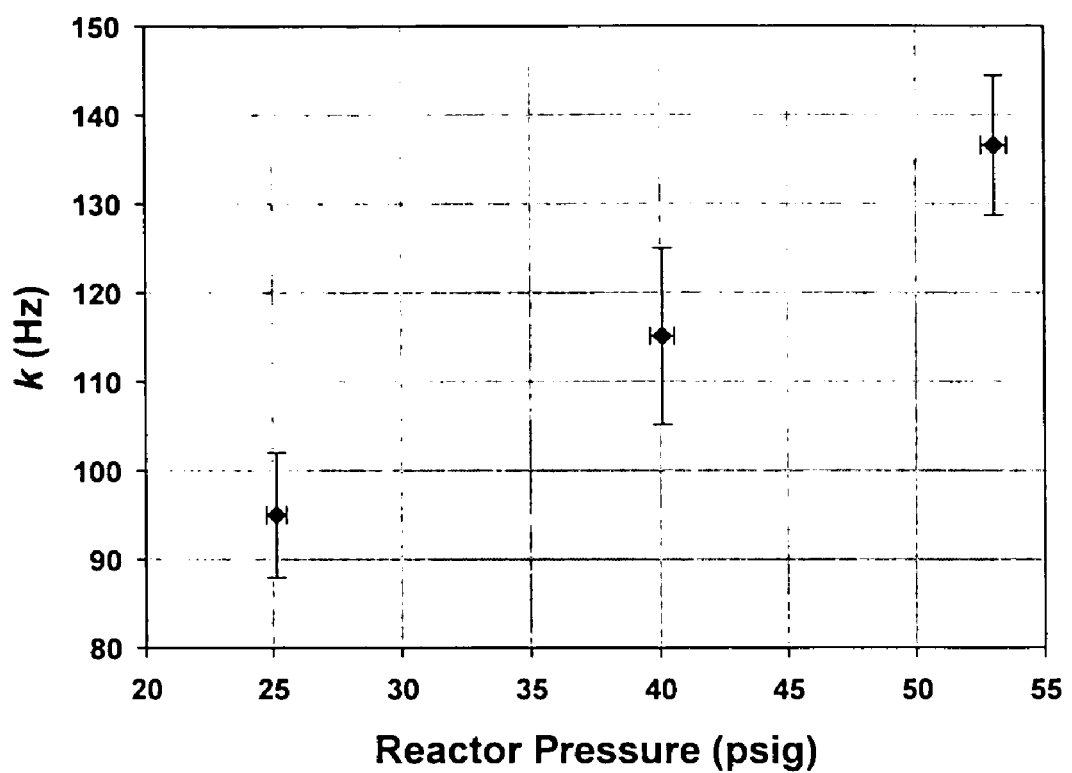
Figure 12: *k* Response to Pressure at 95% Conversion, 930°F, 6% Coke on Catalyst

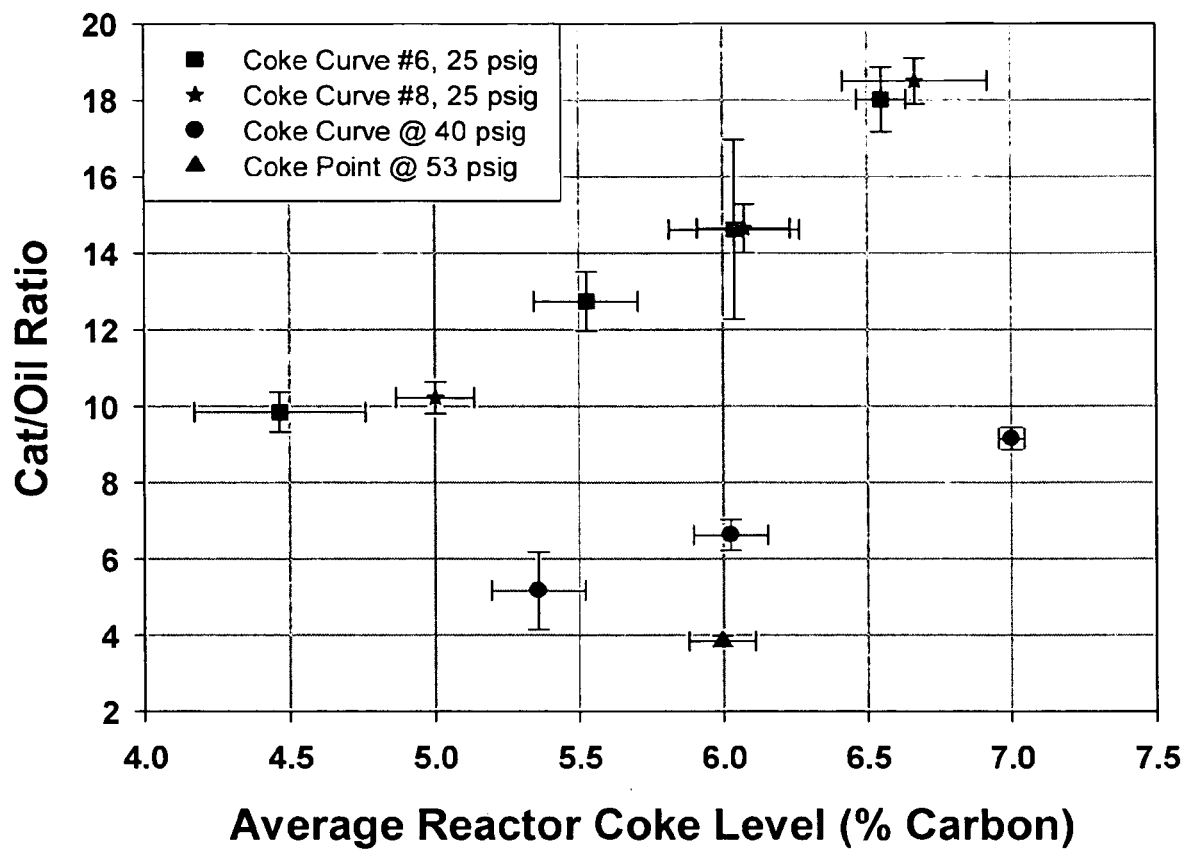
Figure 13: Catalyst Circulation Required for 95% Conversion at 930°F

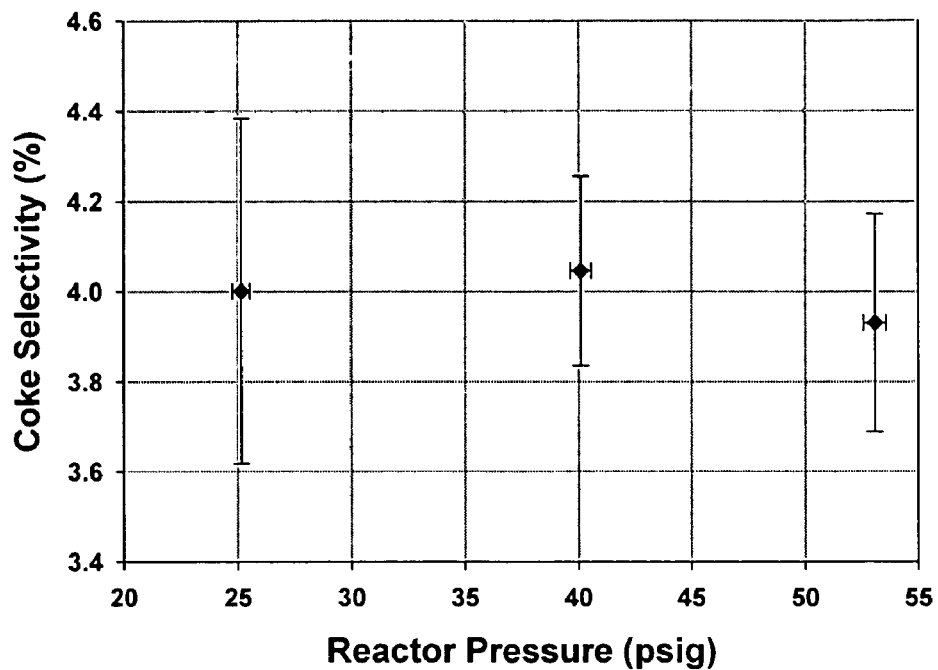
Figure 14: Coke Response to Pressure at 95% Conversion, 930°F, 6% Carbon
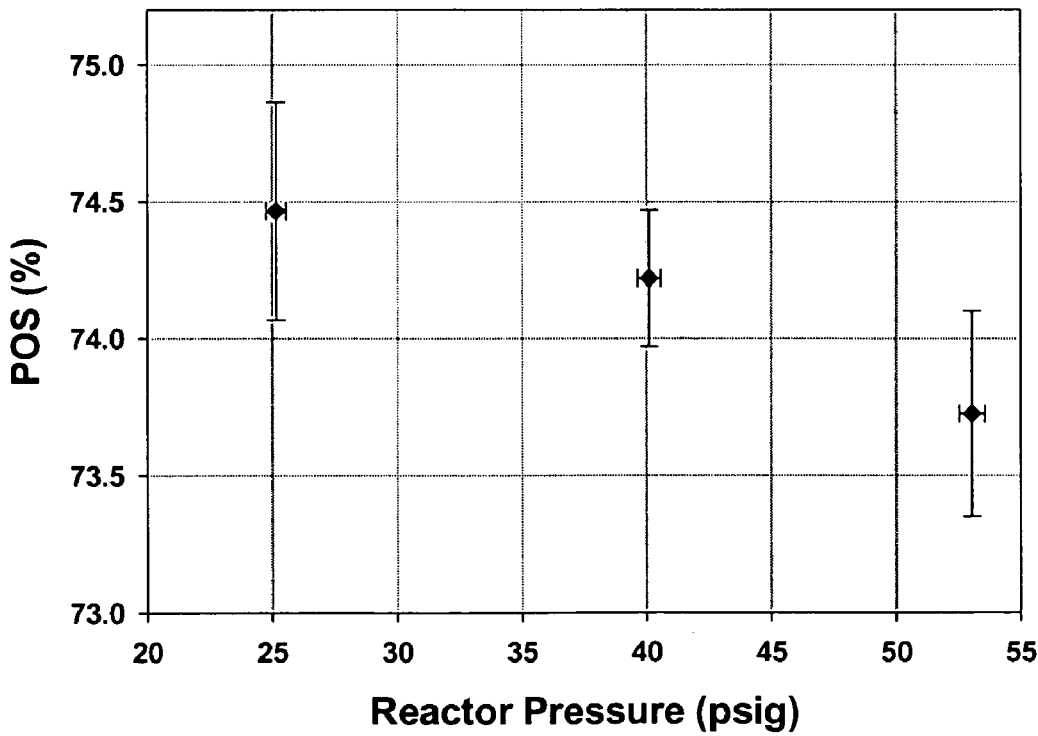
Figure 15: POS Response to Pressure at 95% Conversion, 930°F, 6% Carbon

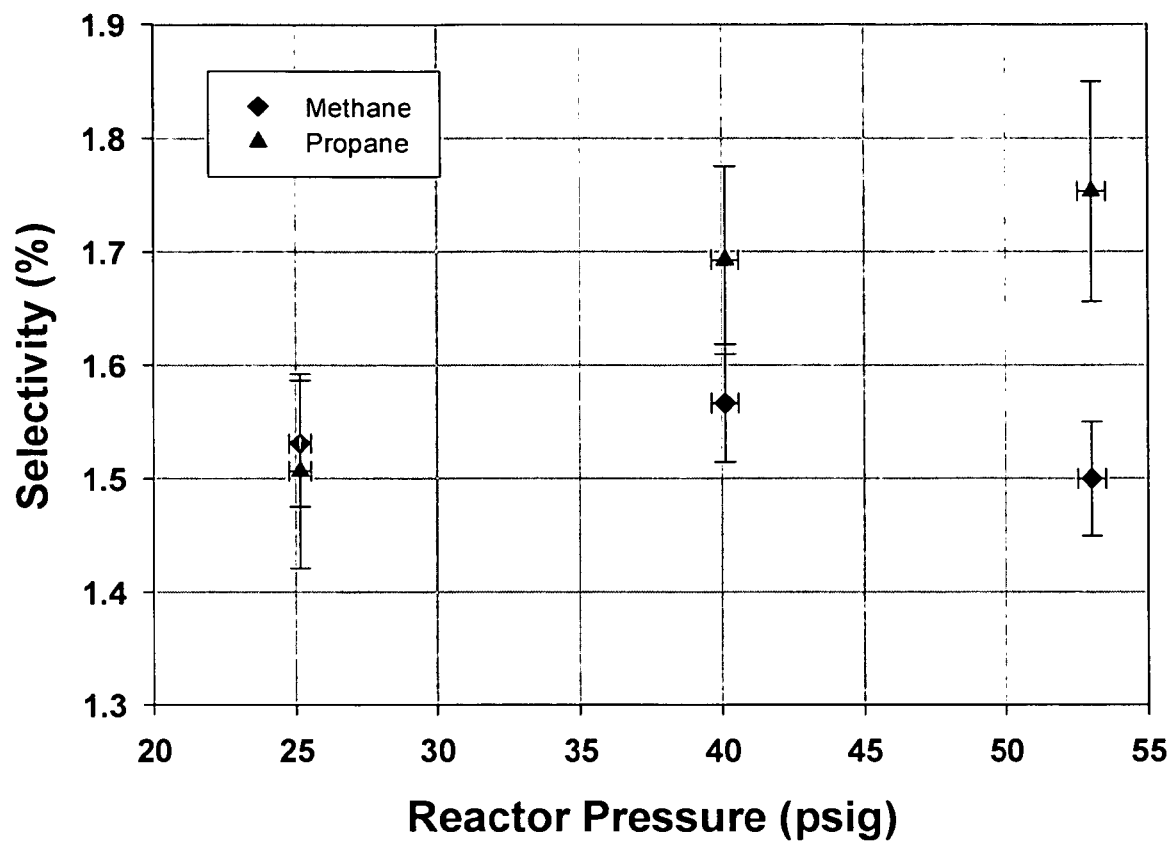
Figure 16: C1 and C3o Response to Pressure at 95% Conversion, 930°F, 6% Coke on Catalyst

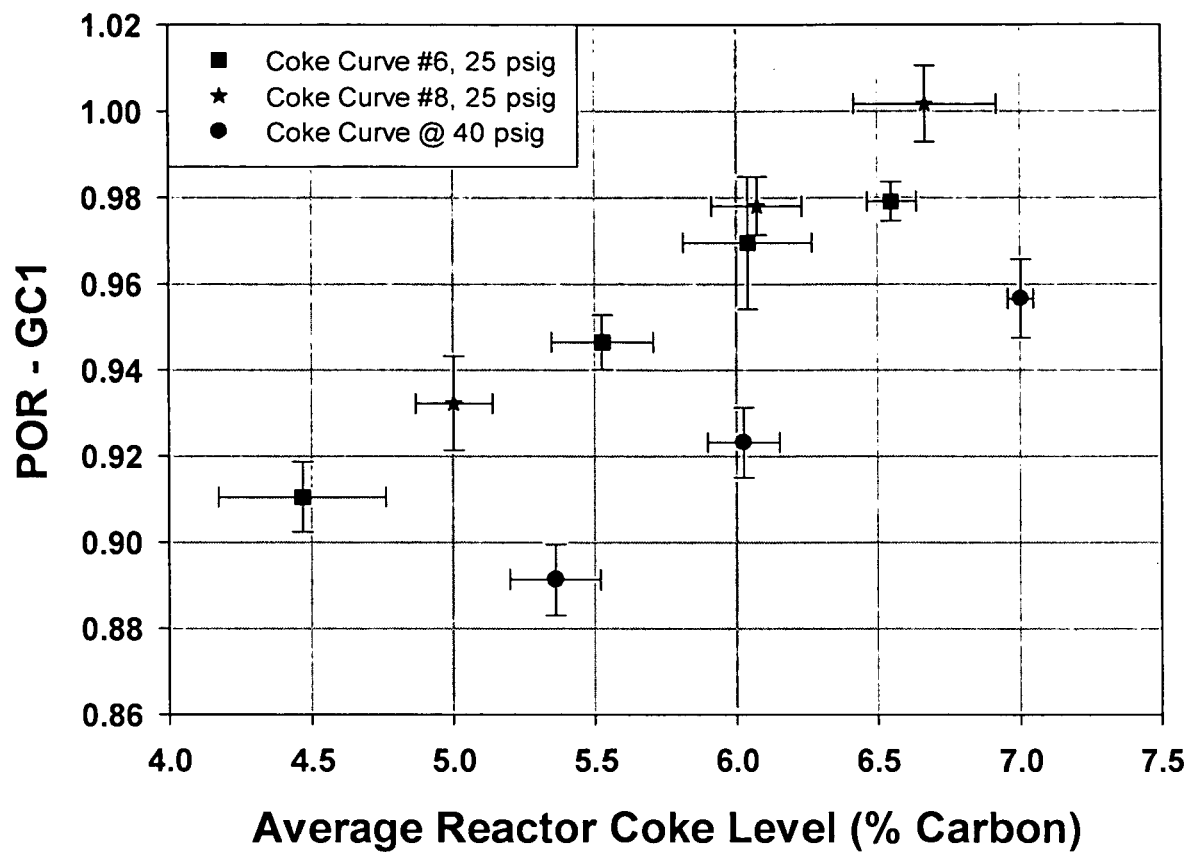
Figure 17: POR Response to Coke at 930°F and 95% Conversion

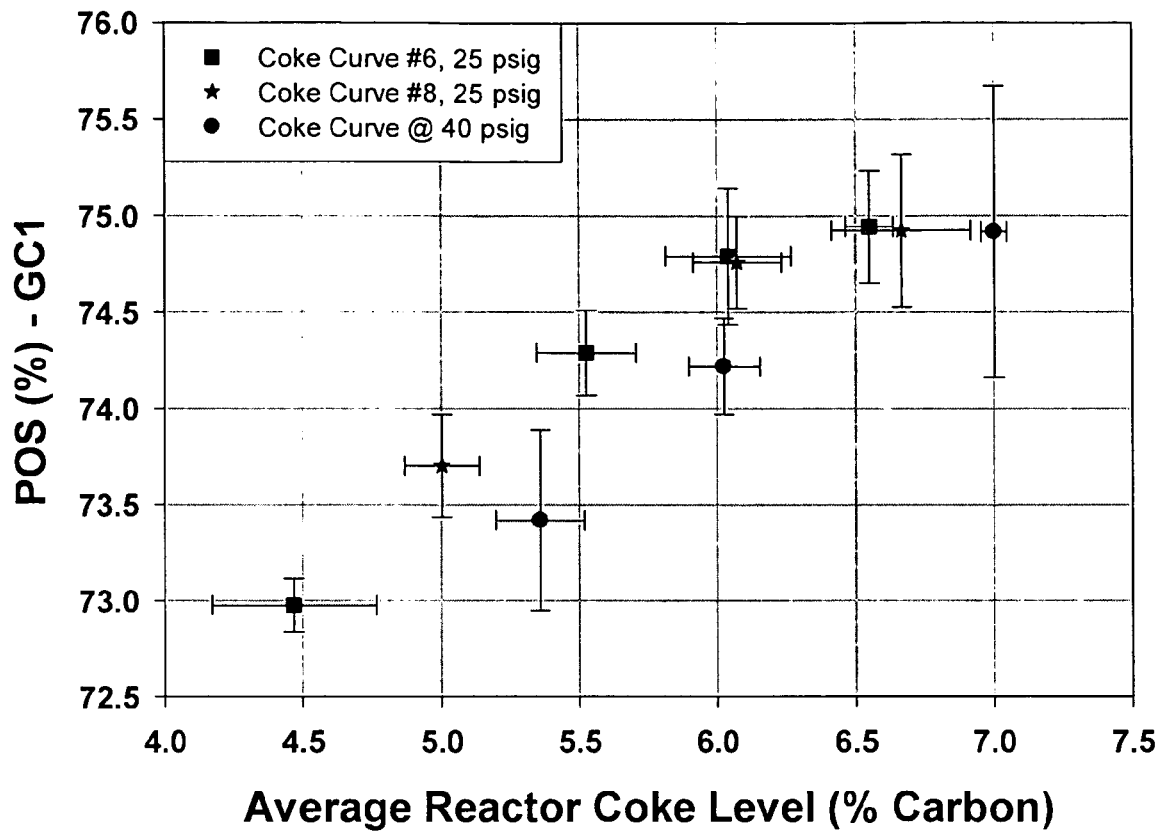
Figure 18: POS Response to Coke at 930°F and 95% Conversion

METHOD OF HIGH PRESSURE AND HIGH CAPACITY OXYGENATE CONVERSION WITH CATALYST EXPOSURE CYCLE

PRIORITY

This application claims priority of U.S. Provisional Application No. 60/788,147, filed Mar. 31, 2006, which is hereby incorporated by reference in its entirety.

FIELD

The present invention relates to a method for converting a feed including an oxygenate to a product including a light olefin. In particular, this invention relates to converting an oxygenate feedstock with a silicoaluminophosphate catalyst to a product including a light olefin in a reaction apparatus in which the catalyst is kept in a continuously moving state through and between a reaction zone and a circulation zone under certain conditions in each zone to achieve remarkable reactor productivity.

BACKGROUND

The production of ethylene and propylene, herein referred to as "light olefins" or "prime olefins," is typically conducted at very large scales to achieve efficient economy of operation, on the order of multiple hundreds of thousands and even multiple millions of metric tonnes per year. This has been a subject of great interest in the emerging field of olefin production via oxygenate conversion with molecular sieve catalysts, especially silicoaluminophosphate (SAPO) molecular sieves, and a number methods have been provided to achieve large volume production with the minimum amount of equipment. However, these methods have had to manage certain characteristics associated with catalysis, most notably rather low relative activities required to obtain desirable reaction selectivities. EP1299504A2 and US2004/0104148 are exemplary references in this regard, resorting to multiple reaction zone conduits or irregular geometries.

When converting oxygenates to a light olefin product, it has been problematic to maximize the production of light olefins, and to control, typically to minimize, the production of by-products, such as light saturates and $C^{5+}$ compounds. In conventional oxygenate conversion processes, high pressure conversion is problematic in terms of a resultant poor yield slate. In these conventional processes, high total pressure is used together with relatively low partial pressure of oxygenate, e.g., they call for one to use a large amount of a substantially inert diluent. U.S. Pat. No. 6,441,261 shows poor activity maintenance at high partial pressures of methanol, and recommends using large amounts of a diluent such as steam to achieve a low partial pressure of oxygenate at a high total pressure of reaction to achieve satisfactory catalytic performance. U.S. Pat. No. 5,126,308 calls for the use of non-steam inert diluent to prevent long term loss of inherent catalyst activity at total reactor pressures up to 250 psig, but provides no catalytic performance data at relatively high oxygenate partial pressures. U.S. Pat. No. 5,811,621 notes total reactor pressures of up to 20 atmospheres, but calls for staged injection of methanol through a series of individual reactors to maintain very low oxygenate partial pressures, an expensive prospect given the very low productivity of olefins for a given volume of reactor and catalyst.

U.S. Pat. No. 4,814,541 discusses conducting high pressure reactions with oxygenates in a slurry of low volatility, high molecular weight diluent, and provide limited performance data for such systems further comprising large amounts of water diluent. While the partial pressure of oxygenate in the data provided is relatively high, the disclosed conversions are quite low. Typically, relative activity declines significantly with increasing oxygenate partial pressure in traditional reaction techniques.

Other methods of conducting oxygenate conversion with silicoaluminophosphate (SAPO) catalysts have been disclosed using high partial pressures of oxygenates, such as U.S. Pat. No. 6,531,639, which indicates advantages for increasing reaction WHSV when increasing oxygenate partial pressure. However, the data provided in that patent also show the relative activity decline of the SAPO catalyst with increasing partial pressure.

Other references such as U.S. Pat. No. 6,673,978, disclose an increase the residence time of catalyst in the reaction zone relative to that in the circulation zone because of detrimental catalyst degradation products generated in the circulation zone. Moreover, U.S. Pat. No. 6,613,950, which similarly directs one increase the residence time of catalyst in the reaction zone relative to that in the circulation zone in order to decrease coke make, also discloses the use of catalysts of very high acidity, that is, having a very high $Si/Al_2$ ratio, which can lead to high coke yields.

It would be desirable to produce as much olefin as practical through a given volume of the reactor while maintaining olefin selectivity, thus higher oxygenate concentrations. The operation of an oxygenate conversion reaction at relatively high oxygenate partial pressures, e.g., in excess of 20 psia, and particularly in excess of 40 psia, would be of great interest if desirable reaction yields could be achieved. It would also be desirable to increase activity maintenance over the course of an oxygenate conversion reaction, e.g. by reducing coke yield. In particular, increasing apparent catalyst activity at a given modest acidity would be desired without resorting to increasing alumina ($Si/Al_2$) ratios, which while increasing inherent catalyst activity tends to provide excessive coke yields. Solving this problem would allow for less catalyst needed and much lower catalyst circulation rates, which would decrease the physical attrition of catalyst and allow for greater production of desired olefins with a lower number of catalyst circulation conduits. Solving both problems simultaneously would provide for a more cost effective and potentially much simpler reaction system with an advantageous yield slate.

DESCRIPTION OF FIGURES

FIGS. 12-18 show plots of experimental results from Example 5 using the large pilot plant oxygenate conversion system of method of the present invention, as described more in detail below.

SUMMARY OF THE INVENTION

Figure 1:
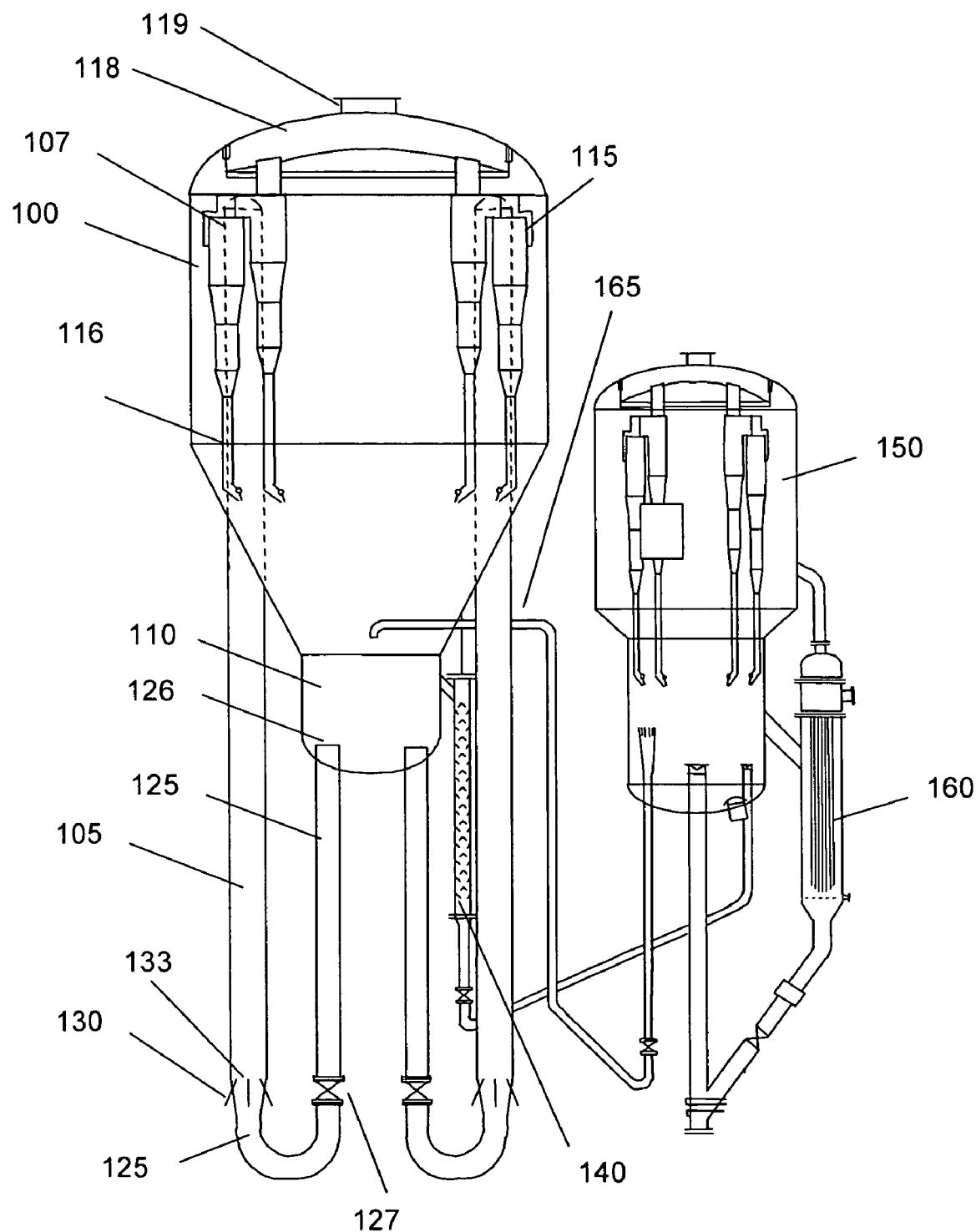
FIG. 1 schematically shows a reaction system according to an embodiment of the invention.

One embodiment of the present invention is directed to a method for conducting an oxygenate conversion reaction comprising: providing an oxygenate feedstock, and a reactor apparatus that includes a reaction zone in fluid communication with a circulation zone, wherein said reaction zone has an inlet and an outlet, and said circulation zone has an inlet, an outlet and a transition zone, said transition zone including one or more displacing gas inlets; contacting the oxygenate feedstock with a catalytically effective amount of a gas-displaced catalyst in the reaction zone under oxygenate conversion conditions to form a product containing light olefins and an oxygenate-exposed catalyst, wherein the gas-displaced catalyst incorporates a silicoaluminophosphate molecular sieve with a Si/Al2 ratio of at least 0.10 and no greater than 0.32, and the conditions include an oxygenate partial pressure in the reaction zone of at least 45 psi (310 kPa) and a reactor gas superficial velocity of at least 10 ft/s (3.0 m/s) at least one point in the reaction zone such that the oxygenate-exposed catalyst is conveyed through the reaction zone to the outlet of the reaction zone, providing at least a portion of the oxygenate-exposed catalyst from the outlet of the reaction zone to the inlet of the circulation zone, and passing the oxygenate-exposed catalyst through the transition zone while flowing a displacing gas from the one or more displacing gas inlets of the transition zone countercurrently through the oxygenate-exposed catalyst in the transition zone, the displacing gas having a superficial velocity of at least 0.1 ft/s (0.03 m/s) at least one point in the transition zone, to form the gas-displaced catalyst; providing at least a portion of the gas-displaced catalyst from the transition zone to the outlet of the circulation zone; and providing at least of portion of the gas-displaced catalyst from the outlet of the circulation zone to the inlet of the reaction zone to be at least a portion of catalyst for the contacting. Conveniently, the contacting is the initial contacting near the inlet of the reaction zone.

In another embodiment, the catalyst in the transition zone remains within the reaction zone for a certain reaction zone residence time, and catalyst in the reaction zone remains within the transition zone for a certain transition zone residence time, such that the transition zone residence time is at least two times, or at least three times the reaction zone residence time.

In other embodiments, the Si/Al$_2$ ratio may be at least 0.12 and no greater than 0.30. The silicoaluminophosphate molecular sieve may comprise SAPO-34, SAPO-18, or both, or may comprise only SAPO-18, SAPO-34 or a combination thereof. Optional embodiments hold that the oxygenate partial pressure may be at least 50 psia (345 kPaa) at least one point in the reaction zone, or at least 45 psia (310 kPaa) and not greater than 200 psia (1380 kPaa) at least one point in the reaction zone. In a particular embodiment, the reaction zone has a total pressure, and the total reactor pressure is at least 45 psia (310 kPaa) and no greater than 200 psia (1380 kPaa) at least one point in the reaction zone.

In yet other embodiments, the reactor gas superficial velocity may be at least 20 ft/s (6.1 m/s) near the inlet of the reaction zone, or at least 15 ft/s (4.6 m/s) at all points in the reaction zone. Additionally or alternatively, the displacing gas superficial velocity may be at least 0.16 ft/s (0.05 m/s) at least one point in the transition zone, or at least 0.1 ft/s (0.03 m/s) at all points the transition zone, or at least 0.1 ft/s (0.03 m/s) and no greater than 1.3 ft/s (0.40 m/s) at all points the transition zone.

In other embodiments, at least 80%, or at least 85%, or at least 90%, or at least 92%, or at least 95 wt. % of the gas-displaced catalyst from the transition zone of the circulation zone is provided to the inlet of the reaction zone to be at least a portion of the catalyst for the contacting. In other embodiments, no greater than 5%, or no greater than 1%, or no greater than 0.1%, or preferably no greater than 0.01% of the oxygenate-exposed catalyst flowing through the reactor outlet into the circulation zone are carried out of the reactor apparatus with the product including a light olefin.

Still other embodiments may have an oxygenate conversion of at least 92 wt % as measured at the reactor outlet, or a weight hourly space velocity based on the silicoaluminophosphate molecular sieve of at least 25 hr$^{-1}$.

In other embodiments, the transition zone further comprises a plurality of baffle layers, and further that an orientation of a first baffle layer is rotated by 90 degrees relative to an orientation of a second baffle layer.

Additionally, the reactor apparatus may comprise a plurality of reaction zones, and the circulation zone comprises a single transition zone and a further includes a plurality of standpipes equal in number to the reaction zones, with each standpipe having a discrete circulation zone outlet in fluid communication with a reaction zone inlet. Conveniently, the reactor apparatus may comprise a single reaction zone, and the circulation zone comprises a single transition zone and no more than two standpipes in fluid communication with the single reaction zone to return the catalyst to the single reaction zone.

In a further embodiment of the present invention, at least one of the light olefins produced is polymerized to form a polymer product.

DETAILED DESCRIPTION

Overview

The present invention is based in part on the discovery that correlating high oxygenate pressure with increased time in the circulation zone maintains a high relative activity of the catalyst and high olefin selectivity. The method of the present invention surprisingly and dramatically enhances the relative activity of the catalyst at high oxygenate partial pressures above those provided by methods in U.S. Pat. No. 6,531,639, does so without decreasing coke yield as provided by methods in U.S. Pat. No. 6,613,950, and does not suffer the yield debit indicated by U.S. Pat. No. 6,673,978. The present invention may be used to design and operate simple, inexpensive oxygenate conversion reactors capable of very high volumes of olefin production, for example, capable of 1 to 1.2 million of tonnes per year of ethylene, or 2 to 2.4 million tonnes per year of ethylene and propylene, or more, in a single riser reactor with only one or two circulation conduits.

When converting oxygenates to a light olefin product, it is desirable to maximize the production of light olefins, and to control, typically to minimize, the production of by-products, such as light saturates, $C_5^+$ compounds, and particularly carbonaceous materials which form on the catalyst and reduces catalyst activity, typically called "coke." In an embodiment, the invention can efficiently produce as much olefin as practical through a given volume of a circulating catalyst fluidized bed reactor while maintaining high catalyst activity and light olefin selectivity. This is achieved by applying a certain inert gas displacement technique, or stripping action, to the catalyst as it circulates between the reaction zone and the circulation zone of the fluidized bed reactor, with certain catalysts and reaction zone conditions peculiarly amenable to such a gas displacement technique.

In one embodiment of the present invention, a feed, including an oxygenate and any diluents, is contacted in a reaction zone with a SAPO bearing, gas-displaced catalyst at effective process conditions to produce a product including light olefins. These process conditions include an effective temperature, pressure, WHSV (weight hourly space velocity), gas superficial velocity and, optionally, an effective amount of diluent, effective for producing light olefins. After exiting the reaction zone the gas-displaced catalyst, having been exposed to oxygenate feedstock, is provided to a circulation zone where the oxygenate-exposed catalyst is separated from the product and subjected to the appropriate stripping action, in particular in a transition zone that is a part of the circulation zone, and the stripped (inert gas-displaced) catalyst is then returned to the reaction zone to contact oxygenate feedstock. These feedstocks, catalysts, process conditions, circulating catalyst fluidized bed reactor elements and stripping conditions are described below in detail.

Oxygenate Feedstock

The oxygenate feedstock of this invention comprises at least one organic compound which contains at least one oxygen atom, such as aliphatic alcohols, ethers, or carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$-$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The feedstock, in one embodiment, may contain one or more diluent(s), typically used to reduce the concentration of the feedstock and hence the oxygenate partial pressure in the reaction zone, and are generally but not necessarily non-reactive to the feedstock or molecular sieve catalyst composition. Non-limiting examples of diluents include helium, argon, nitrogen, carbon monoxide, carbon dioxide, water (or steam), essentially non-reactive paraffins (especially alkanes such as methane, ethane, and propane), essentially non-reactive aromatic compounds, and mixtures thereof. In another embodiment, diluents include other hydrocarbons (which may have some reactivity) present in an oxygenate feedstock either directly or indirectly, and include olefin(s), paraffin(s), aromatic(s) (see, for example, U.S. Pat. No. 4,677,242) or mixtures thereof, preferably propylene, butylene, pentylene, and other hydrocarbons having 4 or more carbon atoms, or mixtures thereof. The most preferred diluents are water and nitrogen, with water in the vapor state (steam) being particularly preferred. The diluent is generally either incorporated directly with an oxygenate feedstock entering into a reactor or added separately and directly into a reactor.

In one embodiment of the invention, the total oxygenate feedstock to the reaction zone may comprise at least 85.0, alternately 90.0, alternately 92.0, alternately 95.0, alternately 98.0, alternately 99.0, and alternately 99.5 wt % oxygenate, the balance being some diluent as described herein. In another embodiment, there may be more than one source of oxygenate feedstock combined to produce the total oxygenate feedstock, for example, a primary feedstock comprising a majority of the oxygenate and an oxygenate recycle, e.g., unreacted oxygenate or other valuable oxygenates produced by the reaction and recovered from the oxygenate reaction effluent product. Desirably, the majority of the total oxygenate feedstock to the reaction zone, such as at least 80 wt %, or at least 90 wt %, or at least 95 wt % of the total oxygenate feedstock to the reaction zone, is US Grade AA Methanol containing at least 99.85 wt. % methanol. In order to produce as much olefin as practical through a given volume of the reactor. Higher concentrations of oxygenate are desirable to this end.

While not preferred, in an alternative embodiment, the oxygenate feedstock utilized in the method of the present invention can be partially converted in another oxygenate conversion process. For example, an oxygenate feedstock comprising mainly oxygenate can be partially converted using utilizing a technique outside the scope of the present invention, say utilizing a different catalyst or a different process that does not involve the appropriate gas displacement action, and that partially converted oxygenate feedstock then utilized in the method of the present invention. The remaining oxygenate in such partially converted oxygenate feedstock would be used in determining the oxygenate partial pressure in the reaction zone (and the hydrocarbons produced counted as diluent).

Catalysts

As used herein, the broad term "catalyst" refers to a gas diplaced catalyst, an oxygenate-exposed catalyst, fresh catalyst (typically, catalyst that has neither been gas-displaced or oxygenate exposed, in particular catalyst that has been recently manufactured) provided to or otherwise within the reactor apparatus, a regenerated catalyst provided to or otherwise within the reactor apparatus, or any combination thereof. The catalyst suitable for catalyzing the oxygenate-to-olefin conversion reaction of the present invention includes a silicoaluminophosphate molecular sieve ("SAPOs") and mixtures of silicoaluminophosphate molecular sieves. Desired silicoaluminophosphate molecular sieves for use with the process of the present invention include "small" and "medium" pore molecular sieves. "Small pore" molecular sieves are defined as molecular sieves with pores having a diameter of less than about 5.0 Angstroms. "Medium pore" molecular sieves are defined as molecular sieves with pores having a diameter from about 5.0 to about 10.0 Angstroms.

SAPOs comprise a three-dimensional microporous crystal framework structure of $[SiO_2]$, $[AlO_2]$ and $[PO_2]$ tetrahedral units. The way Si is incorporated into the structure can be determined by 29Si MAS NMR. See Blackwell and Patton, J. Phys. Chem., 92, 3965 (1988). The desired SAPO molecular sieves will exhibit one or more peaks in the 29Si MAS NMR, with a chemical shift [(Si)] in the range of −88 to −96 ppm and with a combined peak area in that range of at least 20% of the total peak area of all peaks with a chemical shift [(Si)] in the range of −88 ppm to −115 ppm, where the [(Si)] chemical shifts refer to external tetramethylsilane (TMS).

Silicoaluminophosphate molecular sieves are generally classified as being microporous materials having 8, 10, or 12 membered ring structures. These ring structures can have an average pore size ranging from about 3.5-15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

In various embodiments, the SAPO molecular sieve may include a $Si/Al_2$ ratio of at least 0.10 and no greater than 0.32, or at least 0.12 and no greater than 0.30, or at least 0.14 and no greater than 0.28, or at least 0.15 and no greater than 0.26. In general, for a SAPO, higher $Si/Al_2$ ratios provide inherently higher activity to convert methanol. However, as the invention is directed to providing and maintaining high catalyst activity, a $Si/Al_2$ ratio of over 0.32 is likely to produce an excessive apparent catalyst activity that will have a disadvantageous yield of byproducts. Further, in general, for a SAPO, lower $Si/Al_2$ ratios provide certain good attributes, such as low coke yield, but also other attributes, such as an inherently low ratio of ethylene to propylene. As one of the consequences of the pressure requirements of the method of the present invention is, all else being equal, a lower ratio of ethylene to propylene, a $Si/Al_2$ ratio of below 0.10 is likely to reduce the potential ethylene to propylene ratio performance to undesirable ranges.

The catalyst may further contain, in certain proportions, binders, fillers, or other material to provide better catalytic performance, attrition resistance, regenerability, and other desired properties. The molecular sieves are made or formulated into catalysts by combining the synthesized molecular sieves with a binder and/or a matrix material to form a molecular sieve catalyst composition or a formulated molecular sieve catalyst composition. This formulated molecular sieve catalyst composition is formed into useful shape and sized particles by conventional techniques such as spray drying, pelletizing, extrusion, and the like. These binder and filler materials are generally catalytically inert, and include but are not limited to compositions such as kaolin and other clays, various forms of rare earth metals, metal oxides, other non-zeolite catalyst components, alumina or alumina sol, titania, zirconia, magnesia, thoria, beryllia, quartz, silica or silica or silica sol, and mixtures thereof. Preferred proportions of SAPO in the catalyst are formulations containing at least 35, alternately at least 40. In concert with the objective of the invention to practically maximize reactor productivity with good light olefin yield, particularly advantageous proportions of SAPO in the catalyst are formulations containing least 45, alternately at least 50, alternately at least 55, alternately at least 60 and alternately at least 65 wt. % SAPO.

The catalyst composition of the present invention, in other embodiments, may include, in addition to a SAPO and/or binders and fillers, one or more other useful zeolitic molecular sieves (generally termed aluminosilicates, which typically include silicon and aluminum but do not include phosphorous in the framework) including, but not limited to, mordenite, chabazite, erionite, ZSM-5, ZSM-34, ZSM-48 and mixtures thereof. Methods of making these zeolite molecular sieves are known in the art and need not be discussed here. Structural types of small pore aluminosilicate molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore aluminosilicate molecular sieves that are suitable for use in this invention include MFI, MEL, MTW, EUO, MTT, HEU, FER, AFO, AEL, TON, and substituted forms thereof. These small and medium pore zeolites are described in greater detail in the Atlas of Zeolite Structural Types, W. M. Meier and D. H. Olsen, Butterworth Heineman, 3rd ed., 1997, the detailed description of which is explicitly incorporated herein by reference.

Process Conditions

In the oxygenate to olefin reaction, a feed containing an oxygenate is contacted in a reaction zone of a reactor apparatus with a SAPO molecular sieve bearing catalyst, including a gas-displaced catalyst, at process conditions effective to produce light olefins, e.g., an effective temperature, total reactor pressure, oxygenate partial pressure, WHSV (weight hour space velocity) and, optionally, an effective amount of diluent, correlated to produce light olefins. Usually, the oxygenate feed is contacted with the catalyst when the oxygenate is in a vapor phase. Alternatively, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions. As used herein, the term reactor or reactor apparatus includes not only commercial scale reactors but also pilot sized reactor units and lab bench scale reactor units.

One important process condition of the method of the present invention is the oxygenate partial pressure in the reaction zone, especially as determined near the inlet of the reaction zone where there is essentially no conversion just as oxygenate feedstock and catalyst make initial contact. For the purposes of this invention, the oxygenate partial pressure in the reaction zone is calculated as the total moles of oxygenate to the reactor apparatus per hour times the total reaction zone pressure, that product divided by the total number of moles of all oxygenate feedstock species to the reactor apparatus per hour (including diluent). In the event a total pressure gradient exists in the reaction zone, the total reaction zone pressure is the highest pressure in the reaction zone, usually at a reaction zone inlet. In the event of multiple reactor inlet locations, the moles of oxygenate feed to the reactor is determined as the sum of the moles of oxygenates to all inlets to the reactor apparatus per hour, and the total moles of all species is determined as the sum of all the moles of species to all inlets to the reactor apparatus per hour.

In an embodiment, the oxygenate partial pressure in the reaction zone is at least about 45 psi (310 kPa). While not wishing to be bound by theory, this is the oxygenate partial pressure in the reaction zone at which the synergistic impact of oxygenate partial pressure, higher reactor gas superficial velocity and stripping action in the circulation zone achieves high reactor productivity and catalyst activity, at good light olefin selectivity and advantageously low coke make. In other embodiments, the oxygenate partial pressure in the reaction zone is at least 50 psi (345 kPa), or at least 55 psi (380 kPa), or at least 60 psi (415 kPa), or at least 65 psi (445 kPa), or at least 70 psi (480 kPa), or at least 75 psi (515 kPa), or at least 80 psi (550 kPa), or at least 90 psi (620 kPa).

In general, higher oxygenate partial pressures in the reaction zone in the method of the present invention will result in improved reactor productivity and higher apparent catalyst activity, but at certain levels will provide disdvantageous effects, such as excessively high reactor gas superficial velocities (and correspondingly excessively high WHSV) required to maintain a given oxygenate conversion (and hence very high reactor exotherms) and exceedingly low ethylene to propylene ratio in the oxygenate conversion product. Thus, in other various embodiments, the oxygenate partial pressure in the reaction zone is at least 45 psi (310 kPa) and no greater than 200 psi (1380 kPa), or at least 50 psi (345 kPa) and no greater than 180 psi (1240 kPa), at least 55 psi (310 kPa) and no greater than 180 psi (1240 kPa), or at least 60 psi (310 kPa) and no greater than 150 psi (1035 kPa), or at least 65 psi (310 kPa) and no greater than 120 psi (825 kPa).

The total reactor pressure within the reaction zone can vary over a wide range pursuant to providing the oxygenate partial pressures noted herein; this pressure reflects all vapor species within the reaction zone, including diluents and products. In various embodiments, the total reactor pressure is at least 45 psia (310 kPaa), at least 50 psia (345 kPaa), or at least 55 psia (380 kPaa), or at least 60 psia (415 kPaa), or at least 65 psia (445 kPaa), or at least 70 psia (480 kPaa), or at least 75 psia (515 kPaa), or at least 80 psi (550 kPaa), or at least 90 psi (620 kPaa) at least one point in the reaction zone. In various embodiments, the total reactor pressure is at least 45 psia (310 kPaa), at least 50 psia (345 kPaa), or at least 55 psia (380 kPaa), or at least 60 psia (415 kPaa), or at least 65 psia (445 kPaa), or at least 70 psia (480 kPaa), or at least 75 psia (515 kPaa), or at least 80 psi (550 kPaa), or at least 90 psi (620 kPaa) at all points in the reaction zone. In another array of possible embodiments, the total reactor pressure at all points in the reaction zone is no greater than 20 psi, or no greater than 10 psi, or no greater than 5 psi higher than the oxygenate partial pressure in the reaction zone.

In a method of the present invention, the reactor gas superficial velocity (RGSV) in the reaction zone should be sufficient to fluidize the catalyst and convey at least a portion the catalyst in the reaction zone co-currently through the reaction zone to the circulation zone, and promote circulation of the catalyst between the reaction and circulation zones. As used herein and in the claims, the term, "reactor gas superficial velocity," or RGSV, is defined as the combined volumetric flow rate of vaporized oxygenate, diluent (in the feedstock or otherwise) and conversion products, provided to or present in the reaction zone, divided by the cross-sectional area of the reaction zone. Oxygenate is converted to a product including a light olefin while flowing through the reaction zone, and the RGSV may vary at different locations within the reaction zone depending on the total number of moles of gas present (potentially as the result of multiple oxygenate feedstock or diluent inlets to the reaction zone) and the cross sectional area, temperature, pressure and other relevant reaction parameters at a particular location in the reaction zone. In a particular aspect of the present invention, the RGSV is determined near the inlet of the reaction zone where there is essentially no conversion just as the oxygenate feedstock and the catalyst make initial contact. The RGSV near the inlet of the reaction zone is defined as the combined volumetric flow rate of any oxygenate feedstock, including diluent present in the feedstock, provided to the inlet of the reaction zone (whether or not provided in the vapor state), plus any diluent provided to or present in the reaction zone at the reaction zone inlet (for example, via a separate inlet proximate to the oxygenate feedstock inlet, or present in the catalyst provided to the reaction zone inlet from the circulation zone outlet) divided by the cross-sectional area of the reaction zone at the inlet of the reaction zone. If there is more than one oxygenate feedstock or diluent inlet to the reaction zone, the RGSV near the inlet of the reaction zone shall be determined at the inlet furthest removed from the reaction zone outlet (or inlets, if there are multiple inlets about equidistant from the outlet), generally the first place in the reaction zone where gas-displaced catalyst and oxygenate feedstock make initial contact.

Typically, the reactor gas superficial velocity should be at least about 10 feet per second (ft/s) (about 3.0 meters per second, m/s) at least one point in the reaction zone, or conveniently at least about 10 ft/s (3.0 m/s) near the inlet of the reaction zone, or preferably, at least about 10 ft/s (3.0 m/s) at all points in the reaction zone.

In another method of the present invention, the RGSV may be increased above about 10 ft/s (3.0 m/s) to more closely approach a plug flow hydrodynamic flow regime in the reaction zone. As the RGSV increases above about 10 ft/s (about 3.0 m/s), a reduction in axial diffusion, or backmixing, of the gases flowing through the reactor results from a reduction in internal circulation of solids, which carry gas with them. (Ideal plug flow behavior occurs when elements of the homogeneous fluid reactant and product move through a reactor as plugs moving parallel to the reactor axis). In general, minimizing the backmixing of the gases in the reactor increases the selectivity to the desired light olefins in the oxygenate conversion reaction. However, specifically, more plug flow behavior tends to minimize the amount of catalyst required in the reaction zone (lower WHSV) to achieve a given level of oxygenate conversion, and higher RGSV tends to reduce the residence time of the catalyst (more specifically, the average residence time of a given weight of catalyst) within the reaction zone, providing the opportunity for additional relative time in the transition zone during the circulation of the catalyst for the peculiar effect of this invention to be realized.

In other embodiments of the present invention, the reactor gas superficial velocity is at least about 12 ft/s (3.7 m/s), or at least about 15 ft/s (4.6 m/s), or at least about 18 ft/s (5.5 m/s), or at least about 21 ft/s (6.4 m/s), or at least about 24 ft/s (7.3 m/s), or at least about 30 ft/s (9.1 m/s), or at least about 35 ft/s (10.7 m/s), or at least about 40 ft/s (12.2 m/s) at least one point in the reaction zone. In other embodiments of the present invention, the reactor gas superficial velocity is at least about 12 ft/s (3.7 m/s), or at least about 15 ft/s (4.6 m/s), or at least about 18 ft/s (5.5 m/s), or at least about 21 ft/s (6.4 m/s), or at least about 24 ft/s (7.3 m/s), or at least about 30 ft/s (9.1 m/s), or at least about 35 ft/s (10.7 m/s), or at least about 40 ft/s (12.2 m/s) near the inlet of the reaction zone. In still other embodiments of the present invention, the reactor gas superficial velocity is at least about 12 ft/s (3.7 m/s), or at least about 15 ft/s (4.6 m/s), or at least about 18 ft/s (5.5 m/s), or at least about 21 ft/s (6.4 m/s), or at least about 24 ft/s (7.3 m/s), or at least about 30 ft/s (9.1 m/s), or at least about 35 ft/s (10.7 m/s), or at least about 40 ft/s (12.2 m/s) at all points in the reaction zone.

In certain embodiments of this invention, the gas and solid particles are flowed through the gas-solids reactor system at a weight hourly space velocity (WHSV) of at least about 20 $hr^{-1}$, or at least about 25 $hr^{-1}$, or at least about 30 $hr^{-1}$, or at least about 40 $hr^{-1}$, or at least about 50 $hr^{-1}$, or at least about 60 $hr^{-1}$, or at least about 75 $hr^{-1}$, or at least about 100 $hr^{-1}$, or at least about 120 $hr^{-1}$. In other aspects, the WHSV is at least about 20 $hr^{-1}$ and no greater than about 200 $hr^{-1}$, is at least about 30 $hr^{-1}$ and no greater than about 180 $hr^{-1}$, is at least about 40 $hr^{-1}$ and no greater than about 160 hr ~1, is at least about 60 $hr^{-1}$ and no greater than about 140 hr ~1. Unless specifically noted otherwise herein, WSHV figures in the text and those used in the claims are defined as the total weight per hour of the oxygenate in the total oxygenate feedstock flowing into the reaction zone divided by the total weight of the active, molecular sieve material residing within the reaction zone (the weight of binders and fillers are excluded from the determination). In general, the WHSV is correlated with many parameters, including temperature, pressure, and inherent molecular sieve activity (typically a function of $Si/Al_2$ ratio, as modified by the average coke on catalyst in the reactor and reaction zone), to achieve a desired conversion of oxygenate in the reaction zone.

The temperature within the reaction zone under which the oxygenate conversion reaction is effected can vary within a wide range within the scope of the present invention. In various embodiments, the temperature at least one point in the reaction zone can be at least 752° F. (400° C.), or at least 797° F. (425° C.), or at least 842° F. (450° C.), or at least 887° F. (475° C.) or at least 914° F. (490° C.). Alternatively, the temperature at all points in the reaction zone can be at least 752° F. (400° C.), or at least 797° F. (425° C.), or at least 842° F. (450° C.), or at least 887° F. (475° C.) or at least 914° F. (490° C.). In other embodiments, the temperature at any point in the reaction zone can be no greater than 1022° F. (550° C.), or no greater than 1004° F. (540° C.), or no greater than 986° F. (530° C.), or no greater than 968° F. (520° C.), or no greater than 950° F. (510° C.) or no greater than 932° F. (500° C.). Alternatively, the temperature at any point in the reaction zone can be at least 752° F. (400° C.) and no greater than 1022° F. (550° C.), or at least 797° F. (425° C.) and no greater than 1004° F. (540° C.), or at least 842° F. (450° C.) and no greater than 986° F. (530° C.). Temperature requirements for the circulation zone are identical in character to those noted for the reaction zone in this paragraph plus 18° F. (10° C.).

In the present invention, oxygenate conversion, referring to the oxygenate species per se and not including any hydrocarbon co-feed, should be maintained sufficiently high to avoid the need for commercially undesirable levels of oxygenate feedstock recycling. While 100% oxygenate conversion is desired for the purpose of potentially completely avoiding oxygenate feedstock recycle, a reduction in undesirable byproducts is observed frequently when the conversion is greater than about 99.5%. Since recycling up to as much as about 50% of the feed can be commercially acceptable, oxygenate conversions from at least about 50% to no greater than about 99.5% are desired. In other embodiments of the present, the oxygenate conversion is no greater than 99, or no greater than 98, or no greater than 96 wt. %. Alternatively, the oxygenate conversion can be at least 85 wt. % and no greater than 99.5 wt. %, or at least 90 wt. % and no greater than 99.5 wt. %, or at least 92 wt. % and no greater than 99 wt. %, or at least 94 wt. % and no greater than 98 wt. %. Oxygenate conversion rates may be maintained in the range of about 50 wt. % to about 99.5 wt. % using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst circulation rate; reactor apparatus configuration; reactor configuration; feed composition; amount of liquid feed relative to vapor feed; degree of catalyst regeneration; and other parameters which affect the conversion. Unless specifically noted otherwise herein, oxygenate conversion figures in the text and those used in the claims are determined based on the total of oxygenate feedstock as provided to the reactor apparatus, and the total effluent of prime olefins, undesirable byproducts and oxygenate feedstock from the reactor apparatus (those effluent oxygenates correlating directly to those provided), regardless of to which particular zone or zones such oxygenates may be introduced or from which zone or zones such effluent may emanate.

Reactor Apparatus and Operation

In the method of the present invention, the conversion of oxygenates to produce light olefins may be carried out in a variety of large scale catalytic reactors, conveniently fluid bed reactors and concurrent riser reactors as described in Fluidization Engineering, D. Kunii and O. Levenspiel, Robert E. Krieger Publishing Co. NY, 1977, subject to additional requirements fully described herein. Additionally, countercurrent free fall reactors may be used in the conversion process. See, for example, U.S. Pat. No. 4,068,136 and Fluidization and Fluid-Particle Systems, pp. 48-59, F. A. Zenz and D. F. Othmer, Reinhold Publishing Corp., NY, 1960.

The reactor apparatus used in the method the present invention will have a reaction zone, typically a volume defined by and enclosed in a solid wall, such as steel, refractory brick, or both. A catalyst incorporating a SAPO molecular sieve will be contacted with an oxygenate feedstock in the reaction zone, and a reaction will take place under conditions described herein to convert the oxygenate(s) to a product including light olefins. The reaction zone will have an inlet, at which the oxygenate feedstock and catalyst, at least a portion of which includes a gas-displaced catalyst formed in the circulation zone and provided to the reaction zone inlet, are introduced to the reaction zone and make initial contact. The prescribed conditions within the reaction zone will provide at some point in the reaction zone materials in the vapor state, conveniently at or near the reaction zone inlet or further at all points within the reaction zone, which vapor materials may be oxygenate, diluent, reaction products, or a combination thereof. These vapor materials, typically as result of a pressure drop along the axial length of the reaction zone, will move at a velocity, termed a reactor gas superficial velocity, to the outlet of the reaction zone. The reactor gas superficial velocity is sufficient to impart momentum effects that result in the vapor materials carrying along with them cocurrently at least a portion of the catalyst introduced to and within the reaction zone. The vapor materials and catalyst move through the reaction zone and ultimately through the reaction zone outlet, the vapor materials now being a product including a light olefin.

Upon moving through the reaction zone outlet, the conversion product and oxygenate-exposed catalyst enter the circulation zone of the reactor apparatus used in the method of the instant invention, through the circulation zone inlet which is in fluid communication with the reaction zone outlet (conveniently, the reaction zone outlet and circulation zone inlet are essentially the same area within the reactor apparatus). The circulation zone is typically a volume defined by and enclosed in a solid wall, such as steel, refractory brick, or both. Further, within or otherwise part of the circulation zone will typically be at least one element that serves to separate the solid catalyst from the vapor materials, such as the product including a light olefins, diluents, and unreacted oxygenate(s). These elements can be, for example, termination vessels and volumes, cyclone separators, filters, and combinations thereof, or other separation elements and means well within the ken of the skilled artisan. The great majority of the vapor materials as the product including a light olefin will typically then exit the reactor apparatus for further processing, while the great majority of solid catalyst will continue through the circulation zone. It is desirable that such elements serving to separate the solid catalyst, particularly oxygenate-exposed catalyst, from the vapor materials, correlated with certain catalyst durability properties, are configured and operated such that no greater than 5%, or no greater than 1%, or no greater than 0.1%, or preferably no greater than 0.01% of the catalyst flowing through the reactor outlet into the circulation zone are carried out of the reactor apparatus with the product including a light olefin.

An element of the circulation zone utilized in the inventive method will be at least one transition zone. Within the transition zone oxygenate-exposed catalyst flows countercurrently to a displacing gas introduced through displacing gas inlets provided with the transition zone. The displacing gas is conveniently a substantially inert material, such as nitrogen or preferably steam, and may also be a substantially inert hydrocarbon, such as an aliphatic hydrocarbon, including methane, ethane, propane, butane, pentane, hexane or the like. The transition zone is configured such that the velocity of the displacing gas moves countercurrently to the catalyst at a velocity, termed a displacing gas superficial velocity, that promotes such countercurrent flow. This countercurrent flow of displacing gas and catalyst serves to strip the catalyst of, for example, any product that is entrained external and other materials that may be contained or generated internal to the catalyst. These entrained or contained materials are carried along with the displacing gas countercurrently to the catalyst through the circulation zone to exit the reactor apparatus, conveniently in combination with the product including a light olefin.

At least a portion of the catalyst, now being a gas-displaced catalyst as a result of passage through the transition zone, continues through the circulation zone, for example through one or more standpipes, to a circulation zone outlet which is in fluid communication with a reaction zone inlet to make contact with an oxygenate feedstock in the reaction zone (conveniently, the circulation zone outlet and reaction zone inlet are essentially the same area within the reactor apparatus). One circulation pass of the catalyst between the reaction zone and the circulation zone is thus completed, and the process may continue for as long as desired.

FIG. 1 schematically shows an embodiment of a reaction system suitable for performing the invention, and an operation according to the method of the present invention follows. In the embodiment shown in FIG. 1, a plurality of riser reactors 105 are provided for performing a gas-solids reaction. A number of oxygenate feedstock inlets 130 are provided for each riser reactor 105, through which flows oxygenate feedstock. Each riser reactor 105 is a reaction zone, with a reaction zone inlet 133 where oxygenate feedstock makes initial contact with catalyst, including gas-displaced catalyst, flowing from the circulation zone outlet 133.

Continuing with FIG. 1, the tops of risers 105 are shown in a dashed line as they are contained within separation vessel 100. The exits near the top of each riser are coupled with cyclone separator stages 115; the area defining the entrance to the cyclones represents both the reaction zone outlets 107 and the circulation zone inlets 107. During operation, the vaporized feedstock and reaction products carry the catalyst, now oxygenate exposed, through each riser 105 into a set of cyclone separator stages 115. Catalyst solids separated out by the cyclone separator stages 115 passes out of the diplegs 116 and toward transition zone 110 of separation vessel 100, while a product including a light olefin passes out the top of cyclone separator stages 115 into plenum 118 and out of the reactor apparatus through product outlet 119. Preferably, a dense fluidized catalyst bed will be formed by the catalyst in the bottom region of transition zone 110 by the introduction of a displacing gas into transition zone 110 (displacing gas inlets to transition zone 110 are omitted for clarity), with the catalyst flowing countercurrently to the displacing gas in transition zone 110, taking with it any entrained product or internal catalyst materials into separation vessel 100. This dense fluidized catalyst bed of gas-displaced catalyst in transition zone 110 feeds gas-displaced catalyst to the standpipe entry locations 126 for the standpipes 125. Gas-displaced catalyst flows (and optionally any fresh or regenerated catalyst that may be introduced to the reaction or circulation zones of the reactor apparatus) through the standpipes 125, through optional slide valves 127, and through circulation zone outlet 133, which in this embodiment is also reaction zone inlet 133, to make initial contact with oxygenate feedstock. The circulation zone is thus the volume and elements through which catalyst flows between circulation zone inlet 107 and circulation zone outlet 133, including cyclone separator stages 115, the volume within separation vessel 100, the transition zone 110, and standpipes 125.

Further with FIG. 1, a portion of the gas-displaced catalyst in the catalyst bed can be diverted to optional regenerator 150 via the conduit containing catalyst stripper 140. Regenerator 150 is optionally provided with a catalyst cooler 160. Regenerated catalyst can be returned to the reactor apparatus via conduit 165. In the embodiment shown in FIG. 1, regenerated catalyst is returned to the top of the transition zone to join the catalyst exiting the cyclone diplegs. More generally, regenerated catalyst can be distributed at the top of the catalyst bed in the transition zone by any conventional catalyst distribution device known in the art.

In an embodiment, the transition zone includes a plurality of baffles that solid catalyst passes around as it moves down through the transition zone. A variety of structures can be used as baffles. For example, the baffles can be a series of bars or other solid structures arranged parallel to each other that span the interior of the transition zone at a given height in the transition zone. In other embodiments, the baffles can be sheds, gratings, packing, or any other suitable solid structures. In an embodiment, multiple levels of baffles can be used. In such an embodiment, the baffles can resemble a series of sheds, gratings, or other solid structures placed in the transition zone for the solid catalyst to pass through. The solid structure portions in each level can be aligned, or the solid structure portions can be offset so that the openings in one level of baffles align with the solid structure portions of the subsequent level. Other arrangements, such as aligning the solid structure portions of baffle levels perpendicular to each other, or rotating the baffles at another angle, can also be selected. In an embodiment, at least 2 levels of baffle structures can be used, or at least 4, or at least 5, or at least 6, or at least 8. In another embodiment, 10 or less levels of baffle structures can be used, or 8 or less, or 6 or less. In still another embodiment, baffles can be arranged in pairs of levels. Within a pair of baffle levels, the baffles in one level can be matched with the baffles in the second level. For example, the baffles in one level can be rotated 90 degrees relative to the second level. Alternatively, the baffles in one level can be offset to align openings in one level with solid portions in the second level.

In an embodiment, the solid structures used to form the baffles can have various geometries. For example, the solid structures can have a rectangular profile, a triangular profile, or any other convenient solid geometry. In another embodiment, the baffles can be in the form of "sheds." The sheds can have a "v-shaped" profile that is inverted so that the catalyst approaches the point of the "v" as the catalyst moves through the transition zone. Preferably, the sheds can also include a small vertical surface at the bottom edges of the inverted v-shape. Various orientations can be selected for the sheds. All of the sheds can be aligned, or each successive level of sheds can be oriented at an offset, such as a 90 degree offset. Similarly, the positioning of the sheds in each level can offset, as noted herein. In still another embodiment, a commercially available packing material such as Koch Glitsch FCC stripper packing can be used as a baffle material.

In an embodiment, the baffles can be perforated, or otherwise have openings to allow gas to pass through the baffle structure. For example, the baffles can have a series of 0.4 inches (in) (1 centimeter, cm) to 1.2 in (3 cm) diameter holes spaced evenly along the length of the baffle, or in more than one row spread evenly along the length of the baffle. The holes can be separated by at least 0.8 in (2 cm), or at least 1.2 in (3 cm), or at least 1.6 in (4 cm). Alternatively, the holes can be 2.4 in (6 cm) or less apart, or 2.0 in (5 cm) or less apart, or 1.6 in (4 cm) or less apart.

In still another embodiment, one or more gas spargers or other diplacing gas inlets can be provided in the transition zone. Preferably, the displacing gas inlets can be located below the lowest level of baffles within the transition zone. Alternatively, the displacing gas inlet structures can serve as the lowest level of baffles within the transition zone.

The flow rate of steam, nitrogen, or other displacing gas out of the displacing gas inlets, such as displacing gas spargers, and through the transition zone can be characterized in terms of a superficial velocity, termed a displacing gas superficial velocity (DGSV). The displacing gas superficial velocity can be determined by taking the total flow rate of displacing gas through the displacing gas inlets and dividing it by the cross sectional area of the transition zone. Dimensionally, this typically corresponds to a flow rate for the gas in the direction perpendicular to the cross-section of the transition zone. Preferably, the DGSV in the transition zone as introduced by the displacing gas inlets is 0.1 ft/s (0.03 m/sec) or greater, or 0.16 ft/s (0.05 m/sec) or greater or 0.3 ft/s (0.10 m/sec) or greater, or 0.5 ft/s (0.15 m/sec) or greater. In another embodiment, the DGSV in the transition zone introduced by the gas spargers is 1.3 ft/s (0.4 m/sec) or less, or 1.0 ft/s (0.3 m/sec) or less, or 0.8 ft/s (0.25 m/sec) or less, or 0.66 ft/s (0.2 m/sec) or less.

Figure 2A:
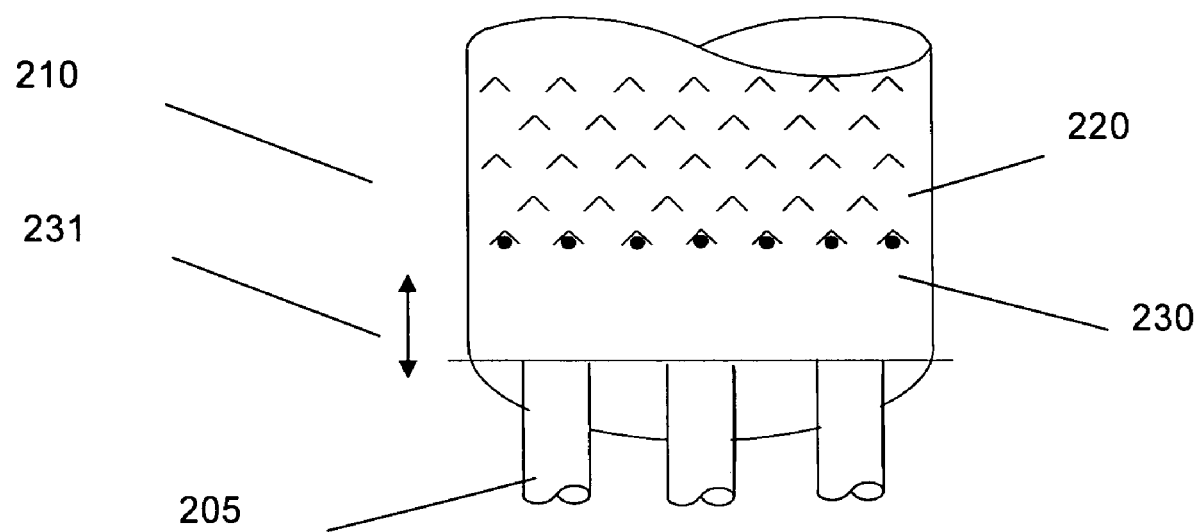
FIGS. 2A and 2B schematically show a portion of a reaction system according to an embodiment of the invention.
Figure 2B:
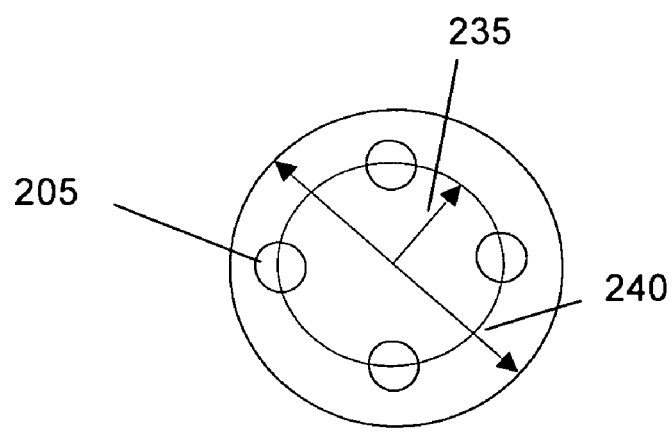

FIGS. 2A and 2B schematically shows an example of a transition zone 210 in a separation vessel according to an embodiment of the invention. FIG. 2A shows a side view of the transition zone 210. In the embodiment shown in FIG. 2A, 5 levels of baffles 220 are used. Each level of baffles is oriented perpendicular to the plane of the drawing. The baffle structures in successive levels are offset from one another, so that an open space in one level is positioned above a baffle structure in the next level. In the embodiment depicted, the baffle structures are inverted v-shaped structures. Preferably, a vertical piece can be attached to the bottom edge of each v-shaped structure. A series of gas spargers 230 is also located underneath the lowest level of baffle structures 220. Preferably, each of the baffle structures 220 is perforated to allow gas to pass through the structures. The gas spargers 230 are separated from the entry locations for the standpipes 205 by a distance 231. In various embodiments, the distance between the gas spargers (or other displacing gas inlets) and the entry locations for the standpipes can be at least 10 in (25 cm), or at least 20 in (50 cm), or at least 30 in (75 cm), or at least 39 in (100 cm). In other embodiments, the distance between the displacing gas spargers (or other gas inlets) and the entry locations for the standpipes can be 118 in (300 cm) or less, or 98 in (250 cm) or less, or 79 in (200 cm) or less. Optional embodiments include the distance between the displacing gas spargers (or other gas inlets) and the entry locations for the standpipes can be at least 10 in (25 cm) and no greater than 118 in (300 cm), or at least 20 in (50 cm) and no greater than 98 in (250 cm), or at least 30 in (75 cm) and no greater than 79 in (200 cm).

Figure 4:
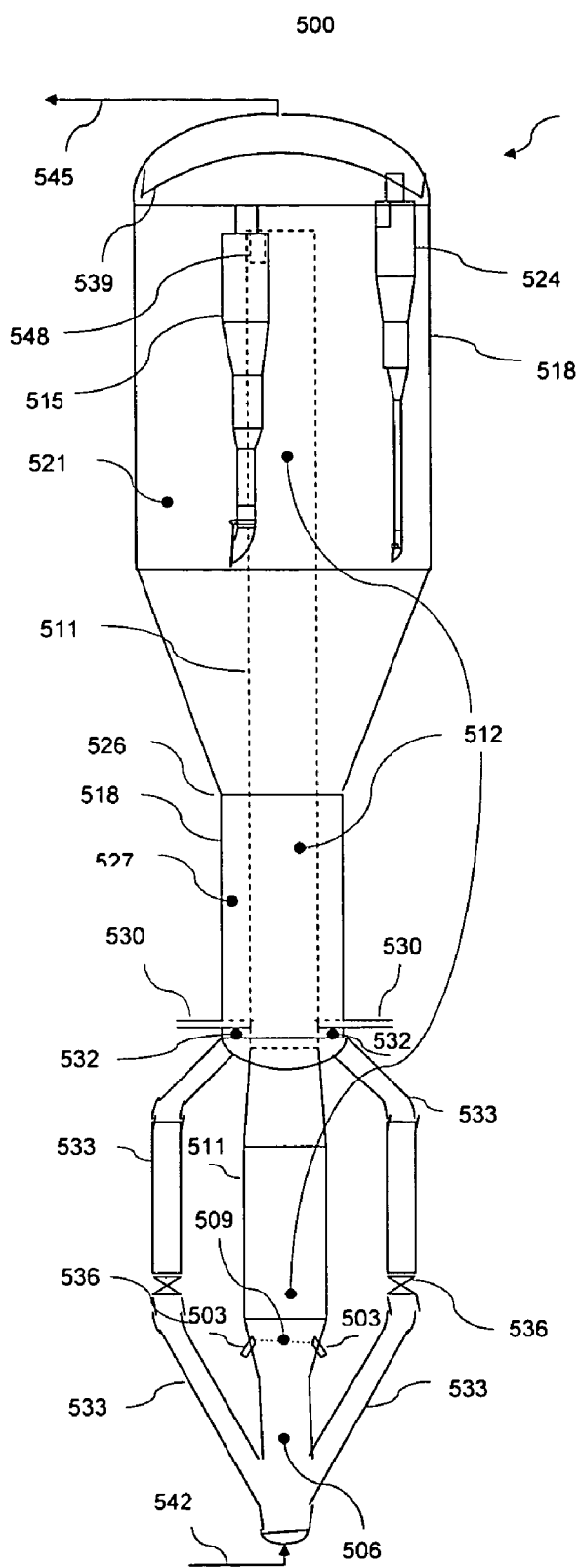
FIG. 4 is a schematic diagram of an embodiment of a reactor apparatus of the present invention.

FIG. 2B depicts a top-down cross-sectional view of the transition zone. As shown in FIG. 2B, 4 standpipes 205 are connected to the separation vessel that includes transition zone 210. FIG. 2B also shows a comparison between a radius 235 from the center of the transition zone 210 to the center of the standpipes 205, and the overall diameter 240 of the transition zone. In this example, the ratio of the radius to the center of the standpipes and the diameter of the transition zone is 0.32. In other embodiments, this ratio can be at least 0.2, or at least 0.25, or at least 0.3. In still other embodiments, this ratio can be 0.4 or less, or 0.35 or less.

In optional embodiments, the density of fluidized material within the transition zone can be at least 20 lb/ft$^3$ (320 kg/m$^3$), or at least 25 lb/ft$^3$ (400 kg/m$^3$), or at least 30 lb/ft$^3$ (480 kg/m$^3$). In other embodiments, the density of the fluidized material in the transition zone can be 50 lb/ft$^3$ (800 kg/m$^3$) or less, 45 lb/ft$^3$ (720 kg/m$^3$) or less, or 40 lb/ft$^3$ (640 kg/m$^3$) or less. Alternatively, the density of fluidized material within the transition zone can be at least 20 lb/ft$^3$ (320 kg/m$^3$) and no greater than 50 lb/ft$^3$ (800 kg/m$^3$), or at least 25 lb/ft$^3$ (400 kg/m$^3$) and no greater than 45 lb/ft$^3$ (720 kg/m$^3$). In various alternative embodiments, the catalyst flux within the transition zone can be 100 lb/ft$^2$*sec (488 kg/m$^2$*sec) or less, or 50 lb/ft$^2$*sec (244 kg/m$^2$*sec) or less, or 35 lb/ft$^2$*sec (170 kg/m$^2$*sec) or less, or 20 lb/ft$^2$*sec (98 kg/m$^2$*sec) or less. In another set of potential embodiments, the catalyst flux within the transition zone can be at least 1 lb/ft$^2$*sec (5 kg/m$^2$*sec), or at least 5 lb/ft$^2$*sec (24 kg/m$^2$*sec), or at least 10 lb/ft$^2$*sec (49 kg/m$^2$*sec). Conveniently, the catalyst flux within the transition zone can be at least 1 lb/ft$^2$*sec (5 kg/m$^2$*sec) and no greater than 100 lb/ft$^2$*sec (488 kg/m$^2$*sec), or at least 5 lb/ft$^2$*sec (24 kg/m$^2$*sec) and no greater than 50 lb/ft$^2$*sec (244 kg/m$^2$*sec), or at least 10 lb/ft$^2$*sec (49 kg/m$^2$*sec) and no greater than 35 lb/ft$^2$*sec (170 kg/m$^2$*sec). The density of fluidized material within the transition zone and catalyst flux within the transition zone will be affected by the selection of catalyst properties (e.g., bulk density and average particle size) and displacing gas superficial velocities, among other parameters described herein (e.g., configuration of the transition zone).

Another metric that can be used in the method of the present invention is the residence time of catalyst within the transition zone. In an embodiment, the residence time for catalyst in the transition zone can be 60 minutes or less, or 10 minutes or less, or 1 minute or less. In another embodiment, the residence time can be at least 5 seconds, or at least 10 seconds, or at least 30 seconds. In other embodiments, the residence time for catalyst in the transition zone is at least about 2 times, or at least about 2.5 times, or at least about 3 times, or at least about 3.5 times, or at least about 4 times, or at least about 5 times, or at least about 6 times the residence time of catalyst in the reaction zone.

The residence time of catalyst in a given zone of the reactor apparatus may be determined by any means known to those skilled in the art, but is typically a tedious calculation requiring a number of empirically developed parameters specific to the type of catalyst, gas superficial velocity and other details of the system employed, resulting in the determination of a volumetric catalyst flow rate, and dividing the applicable volume (e.g., reaction zone or circulation zone) by that rate to determine the average catalyst residence time. ("Catalyst residence time" and "average catalyst residence time" are used interchangeably herein, as typically calculations are made on a bulk basis and represent average times for all catalyst particles rather than a particular time for a discrete catalyst particle). Such detailed determinations can be made for the method of the present invention in determining specific average catalyst residence times within various zones. However, for the purpose of the present invention, within the RSGV and DSVG stipulated and operation typically at steady state with a continuous moving of catalyst between the reaction and circulation zones, the ratio of the residence time of catalyst in one given zone to another given zone can be readily determined as the ratio of the mass of catalyst in the one given zone to the mass of catalyst in the other given zone.

Many means of measuring and calculating the mass of catalyst in a zone of a reactor apparatus of the present invention are well known to those skilled in the art. One simple means comprises a determination of the pressure differential between two different heights in the same element of a given zone in the same direction as gravity while the apparatus is operational in the method of the present invention. The pressure differential is then divided by the difference in the height, which provides an average density within the element. This average density is then multiplied by the volume of the element under consideration, which is known through straightforward geometric calculations based on the design or actual measurements of the element or elements within the zone, which provides a determination of mass in the element. Due to the large difference in the density between the oxygenate feedstock, diluents, and oxygenate conversion products within a zone under consideration and the density of the catalyst within that element, it is permissible to consider that determined mass to be the mass of catalyst within that element. The masses of each element within a zone may be added to determine the total mass within the zone. In the method of the present invention, the catalyst is moved around among the various elements in a random fashion such that an appropriate sample volume of catalyst in any zone or element therein will be very similar, in terms of the proportion of molecular sieve and binders and fillers. Thus there is typically no need to consider the actual proportion of sieve and binders and fillers in the catalyst in making the determination of the mass of the catalyst in the reaction zone and in the circulation zone, even if different proportions are added to the reactor apparatus at different times while employing the method of this invention.

In the present invention, in the event that means to determine the mass of catalyst in certain elements during operation of the reactor apparatus are not available, for example, through the omission of appropriate pressure taps in a cyclone or cyclone diplegs in the design and construction of the reactor apparatus, one should utilize the expected mass of catalyst determined at operating design conditions as specified for the construction or utilization of the reactor apparatus or element in oxygenate conversion service. If no such design or construction specifications or calculations are available, then one should assume for the circulation zone that the entire volume of an element, as determined from as-built geometric measurements, is full of catalyst at its normal, uncalcined bulk density prior to being introduced to the reactor apparatus, and for the reaction zone that 15% of the volume of an element, as determined from as-built geometric measurements, contains catalyst at its normal, uncalcined bulk density prior to being introduced to the reactor apparatus.

Methods of establishing and manipulating the ratio of the mass of catalyst in the reaction zone to that of the sum of the mass of the catalyst in both the reaction zone and the circulation zone using a number of methods well known to those skilled in the art. Example include, but are not limited to, proper selection of one or more of the following: geometry of the various elements of the reactor apparatus, including the reactor vessel, cyclones, diplegs, conduits and transfer lines, and auxiliary equipment such as catalyst coolers and strippers, resulting in various open volumes of the elements into which catalyst might exist; and design and operating conditions in the various elements of the reactor apparatus, including pressure drops across control (typically slide) valves requiring more or less catalyst in the conduits feeding the valves, desired GSV, rate and type of fluffing vapor (which assists catalyst fluidization) in various elements and lift gas in various conduits, and levels of catalyst in various elements; and base activity of the catalyst prior to introduction to the reactor apparatus and the level of coke on the catalyst in the reaction zone during use in the reactor apparatus, each of which will determine how much catalyst is needed in the reaction zone to achieve a desired conversion of oxygenate feedstock, and the desired level of conversion of oxygenate feedstock.

In different embodiments of the present invention, the residence time of catalyst in the reaction zone can be no greater than 30 minutes, or no greater than 10 minutes, or no greater than 5 minutes, or no greater than 1 minute, or no greater than 30 seconds, or no greater than 15 seconds. In other embodiments, the residence time of catalyst in the reaction zone can be at least 1 second, at least 2 seconds, or at least 5 seconds, or at least 10 seconds, or at least 30 seconds. Conveniently, the residence time of the catalyst in the reaction zone is at least 1 second and no greater than 1 minute, or at least 2 seconds and no greater than 30 seconds.

Figure 3:
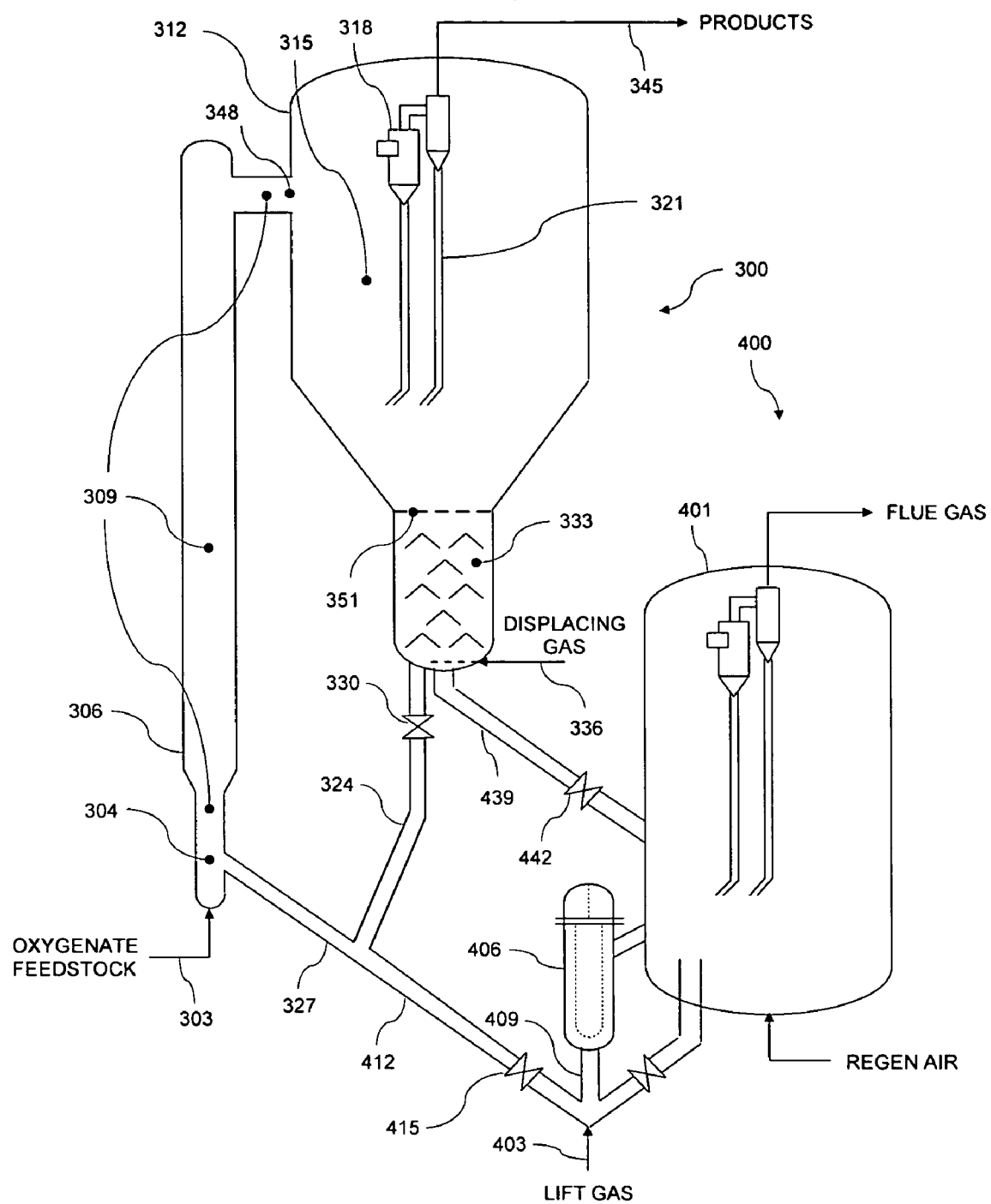
FIG. 3 is a schematic diagram of an embodiment of a reactor apparatus of the present invention.

FIG. 3 is a another schematic diagram of an embodiment of a reactor apparatus 300 utilizing the method of the present invention in conjunction with a catalyst regenerator 400. Oxygenate feedstock, comprising at least some in a vaporized form, is supplied through line 303 to a reactor vessel 306, the reactor vessel including a reaction zone 309 comprising an inlet zone 304, that contains fluidizable SAPO bearing catalyst particles provided from gas-displaced catalyst standpipe 324 and conduit 327 through circulation zone outlet 304 (element 304 serves as both the reaction zone inlet and circulation zone outlet).

Remaining with FIG. 3, an oxygenate conversion reaction takes place in and products including prime olefins are formed in reaction zone 309, and the fluidizable catalyst particles, now oxygenate exposed, are carried into termination vessel 312 through reaction zone outlet 348 (element 348 is also the circulation zone inlet). Termination vessel 312 comprises a termination vessel volume 315, which is one element of the circulation zone, and is the first element of a disengaging zone that eventually leads to products leaving the reactor apparatus altogether through line 345. Termination vessel volume 315 is of substantially larger cross sectional area than the reaction zone, thus significantly slowing the GSV in that termination space and allowing a large portion of the catalyst to settle downward with gravity and become largely separated from the oxygenate conversion products, and any diluent or unconverted oxygenate conversion feedstock that may be present. Another portion of the fluidizable catalyst particles are carried into a cyclone separator device 318, where catalyst is also largely separated from the oxygenate conversion products, and any diluent or unconverted oxygenate conversion feedstock that may be present, and falls into dipleg 321, where it is transferred into termination vessel volume 315. The catalyst in termination vessel volume 315 flows downward through transition zone inlet 351, marked with a dashed line at the demarcation of the cylindrical and conical sections, into transition zone 333.

Still with FIG. 3, a displacing gas is provided through line and sparger 336 to a location near the bottom of transition zone 333, causing the displacing gas to rise through transition zone 333, stripping the catalyst as it falls through transition zone 333. Some contacting devices, e.g., shed trays, are shown in transition zone 333 to facilitate stripping by the displacing gas. A large portion of the gas-displaced catalyst exits transition zone 333 below displacing gas line and sparger 336 to enter and flow through circulation standpipe 324, and subsequently moves through line 327 where it joins regenerated catalyst coming from the regenerator 400 through line 412, and both types of catalyst are lifted against gravity through line 327 (via lift gas provided in line 403) to the reaction zone inlet 304 and to reaction zone 309. Optionally, a control valve 330 may be used on gas-displaced catalyst circulation standpipe 324. The remaining small portion of the gas-displaced catalyst from transition zone 333 may flow through regenerator entry standpipe 439 to catalyst regenerator vessel 401. Optionally, a control valve 442 may be used in regenerator entry standpipe 439. Regenerated catalyst may be returned to reaction zone 309 through the reaction zone inlet zone 304, in this example after having been cooled in catalyst cooler 406, passing through a line 409 in fluid communication with another line 412, and joining with the gas-displaced catalyst from line 324 in line 327. Optionally, a control valve 415 may be used in line 412. The large majority of oxygenate conversion products from the oxygenate conversion reaction in reaction zone 309, gas-displaced products from the transition zone 333, and unconverted oxygenate feedstock or diluents, if any, are removed from the reactor apparatus in line 345. Some small measure of such materials may be introduced into the regenerator 400 due to the imperfect nature of stripping in transition zone 333.

In the embodiment shown in FIG. 3, the circulation zone comprises elements 348 (as both the circulation zone inlet and reaction zone outlet), 315, 318, 351, 333, 336, 330, 324, 327, and 304 (as both the circulation zone outlet and reaction zone inlet). A determination of the residence time of catalyst within transition zone element 333 would be made, in order to develop the appropriate ratio including the residence time of catalyst in the reaction zone 309, which includes inlet zone 304. In general, the volume of the transition zone is that in which the displacing gas superficial velocity is at least 0.03 m/s. In this example, we assume the displacing gas superficial velocity provided by displacing gas from line and sparger 336 is 0.03 m/s in the cylindrical transition zone 333 directly above, and thus the volume of transition zone 333 is the volume encompassed between the sparger 336 and the transition zone inlet 351 (much above transition zone inlet 351, the increased area for flow in termination vessel volume 315 would quickly decrease the displacing gas superficial velocity).

FIG. 4 is a schematic diagram of yet another embodiment of a reactor apparatus 500 utilizing the method of the present invention. Oxygenate feedstock is supplied through nozzles 503 to a reactor vessel 511, the reactor vessel including a reaction zone 512 comprising a lower larger diameter cylinder, a frusto-conical section and a higher smaller diameter cylinder. Reaction zone 512 contains fluidizable, SAPO bearing, gas-displaced catalyst particles provided from lower circulation zone 506 through circulation zone outlet 509 (element 509 also serves as the reaction zone inlet). Catalyst particles in lower circulation zone 506 are fluidized and lifted through circulation zone outlet 509 into reaction zone 512 by the introduction of a fluidization medium, such as steam, through line 542. In this example, the reaction zone inlet is determined to be the area just above where oxygenate feedstock is introduced, as that is the first place in the apparatus where contacting between the oxygenate feedstock and the gas-displaced catalyst can take place.

Continuing with FIG. 4, an oxygenate conversion reaction takes place in and products including prime olefins are formed in reaction zone 512, and the fluidizable particles, now oxygenate exposed, are carried into close coupled, primary cyclone separator 515 through reaction zone outlet 548 (element 548 is also the circulation zone inlet). In general, the reaction zone outlet is determined as the entrance to an element that works to separate catalyst from reaction product, which in this example is reaction zone outlet 548 as the entrance to primary cyclone separator 515.

Remaining with FIG. 4, oxygenate conversion product including light olefins, and any unconverted oxygenate feedstock and diluent that may be present, and a minor amount of catalyst exit the top of primary cyclone separator 515 into termination vessel volume 521 formed by termination vessel 518. The upper portion of termination vessel volume 521 is of substantially larger cross sectional area than the reaction zone, thus significantly slowing the GSV in that termination volume and allowing a large portion of any catalyst that may emanate from the top of primary cyclone 515 to settle downward with gravity and become largely separated from the oxygenate conversion products, and any diluent or unconverted oxygenate conversion feedstock that may be present. Reaction products, and any unconverted oxygenate feedstock and diluent that may be present in termination volume 521, and an even smaller amount of entrained catalyst enter secondary cyclone separator 524. Reaction products, and any unconverted oxygenate feedstock an diluent that may be present, and a very small amount of residual catalyst exit the top of secondary cyclone separator through plenum 539 and exit the reactor apparatus through line 545 for further processing. Alternatively, the top outlet of primary cyclone 515 may be close coupled to the inlet of secondary cyclone 524 so that very little reaction product and other attendant materials flow through termination vessel volume 521.

Still with FIG. 4, catalyst falls into the lower diplegs of primary cyclone separator 515 and secondary cyclone separator 524 into termination vessel volume 521, and along with any catalyst settling from elsewhere in termination vessel volume 521 flows downward through transition zone inlet 526, marked by a solid line at the demarcation of the cylindrical and conical sections of termination vessel 518, into annular transition zone 527, the annulus formed by the lower portion of termination vessel 518 and the higher smaller diameter portion of reactor vessel 511.

Maintaining reference to FIG. 4, a displacing gas is provided through lines and spargers 530 to a location near the bottom of transition zone 527, causing the displacing gas to rise through transition zone 527, stripping the catalyst as it falls through transition zone 527. Some contacting devices, e.g., shed trays, that may be present in transition zone 527 to facilitate stripping by the displacing gas, are not shown. A large portion of the gas-displaced catalyst from transition zone 527 falls into defluidization zone 532, and then enters circulation standpipes 533 and is moved to lower circulation zone 506 on its way back to the reaction zone. Optionally, control valves 536 may be used on gas-displaced catalyst circulation standpipes 533. In a separate embodiment, a small portion of the gas-displaced catalyst from transition zone 527 or elsewhere from the reactor apparatus 500 may flow to a regenerator, and regenerated catalyst from the regenerator may be returned to a desired location in reactor apparatus 500.

In the embodiment shown in FIG. 4, the circulation zone comprises elements 548 (as the circulation zone inlet and reaction zone outlet), 515, 521, 524, 527, 530, 532, 533, 536, 506, 542 and 509 (as both the circulation zone outlet and reaction zone inlet). A determination of the residence time of catalyst within annular transition zone element 527 would be made, in order to develop the appropriate ratio of the residence time of catalyst in transition zone 527 to the residence time of catalyst in reaction zone 512. In general, the volume of the transition zone is that in which the gas superficial velocity of the displacing gas is at least 0.03 m/s. In this instance, we assume the gas superficial velocity of the displacing gas from line and sparger 530 is 0.03 m/s in the annular transition zone 527 directly above, and thus the volume of transition zone 527 is the volume encompassed in the annular space between the lines and spargers 530 and the transition zone inlet 526 (much above transition zone inlet 526, the increased area for flow would quickly decrease the gas superficial velocity).

In one embodiment, the reaction zone may be a single reaction zone and the circulation zone a single circulation zone conduit. In another embodiment, the reaction zone may be a single reaction zone and the circulation zone comprises one or no more than two circulation zones, each zone comprising such elements as standpipes and ancillary conduits or valve, that serve to circulate catalyst back to the reaction zone. In yet another embodiment, the reaction zone may be a single reaction zone, part of which forms an annulus, with that annular region being at least a part of the circulation zone, conveniently at least a part of the transition zone section of the circulation zone. The reaction zone may be a cylinder or frustum including a diameter of at least 8 feet and no greater than 16 feet. The reaction zone may be a frustum with a smaller diameter of at least 8 feet and no greater than 12 feet, and a larger diameter at least 1 foot, 1.5 feet or 2 feet greater than the smaller diameter.

In one embodiment, the circulation zone may include a cylindrical disengaging zone, or separation vessel, with a diameter of at least 30, 35, 40, 50 or 60 feet and no greater than 80 or 75 feet. In another embodiment, the circulation zone may include a cylindrical transition zone in fluid communication with the disengaging zone, and the transition zone may have a diameter of at least 10, 12, 15, or 20 feet and no greater than 25, 30, 35 or 40 feet. In other embodiments, the circulation zone may include a cylindrical standpipe in fluid communication with the transition zone, and the standpipe may have a diameter of at least 20, 22, 24 or 30 inches and no greater than 40, 45, 50 or 55 inches.

In particular embodiments, the rate of contained oxygenate in the feedstock to the single reaction zone may be at least 415,000, or 520,000, or 625,000, or 830,000 kg/hr, desirably in certain other embodiments, also operating within the method of the present invention at the high conversion levels noted above (e.g., at least 85% and no greater than 99.5%).

In yet another embodiment of the invention, the solids particles and gas are flowed through the reaction zone at a solids loading, or density within the reaction zone, of at least 0.1 lb/ft$^3$ (1.6 kg/m$^3$), or at least 0.5 lb/ft$^3$ (8 kg/m$^3$), or at least 1.0 lb/ft$^3$ (16 kg/m$^3$), or at least 2.0 lb/ft$^3$ (32 kg/m$^3$), or at least 4.0 lb/ft$^3$ (64 kg/m$^3$). Alternatively, the solids loading can be 5 lb/ft$^3$ (80 kg/m$^3$) or less, or 4.0 lb/ft$^3$ (64 kg/m$^3$) or less, or 2.0 lb/ft$^3$ (32 kg/m$^3$) or less.

The techniques of this invention are particularly suited to large, commercial scale reactor apparati. For example, the techniques of this invention are particularly suited to reactor apparati that require a catalyst loading of at least about 1,000 kg of catalyst, based on total amount of catalyst located throughout the reaction apparatus. In particular, the method of this invention are particularly suited to reactor apparati that require a catalyst loading of at least about 10,000 kg of catalyst, more particularly a catalyst loading of at least about 100,000 kg of catalyst, and most particularly a catalyst loading of at least about 250,000 kg of catalyst, based on total amount of catalyst located throughout the reaction system.

During the conversion of oxygenates to prime olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. According to another embodiment of the present invention, a portion of the catalyst is withdrawn from the reactor apparatus and is partially, if not fully, regenerated in a regenerator. By regeneration, it is meant that the carbonaceous deposits are at least partially removed from the catalyst. Desirably, the portion of the catalyst withdrawn from the reactor apparatus is at least partially deactivated. The regenerated catalyst, with or without cooling, is then returned to the reactor apparatus.

In still another embodiment, the disengaging vessel also includes a stripping zone, typically in a lower portion of the disengaging vessel. In the stripping zone the coked catalyst composition is contacted with a gas, preferably one or a combination of steam, methane, carbon dioxide, carbon monoxide, hydrogen, or an inert gas such as argon, preferably steam, to recover adsorbed hydrocarbons from the coked catalyst composition. After exiting the separation devices and/or disengaging vessels, some or all of the catalyst can then be introduced to a regeneration system.

In an embodiment, at least a portion of the coked catalyst composition is withdrawn from the reactor apparatus, typically from the circulation zone, and introduced to the regeneration system. The regeneration system comprises a regenerator where the coked catalyst composition is contacted with a regeneration medium, preferably a gas containing oxygen, under conventional regeneration conditions of temperature, pressure and residence time. In an embodiment, a gas-solids flow exiting a regenerator may be passed through cyclone separators.

Non-limiting examples of suitable regeneration media include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. Suitable regeneration conditions are those capable of burning coke from the coked catalyst composition, preferably to a level less than 0.5 weight percent based on the total weight of the coked molecular sieve catalyst composition entering the regeneration system. For example, the regeneration temperature may be in the range of from about 200° C. to about 1500° C., such as from about 300° C. to about 1000° C., for example, from about 450° C. to about 750° C., and conveniently from about 550° C. to about 700° C. The regeneration pressure may be in the range of from about 15 psia (103 kPa) to about 500 psia (3448 kPa), such as from about 20 psia (138 kPa) to about 250 psia (1724 kPa), including from about 25 psia (172 kPa) to about 150 psia (1034 kPa), and conveniently from about 30 psia (207 kPa) to about 60 psia (414 kPa).

The residence time of the catalyst composition in the regenerator may be in the range of from about one minute to several hours, such as from about one minute to 100 minutes. The amount of oxygen in the regeneration flue gas (i.e., gas which leaves the regenerator) may be in the range of from about 0.01 mole percent to about 5 mole percent based on the total volume of the gas. The amount of oxygen in the gas used to regenerate the coked catalyst (i.e., fresh or feed gas) is typically at least about 15 mole percent, preferably at least about 20 mole percent, and more preferably from about 20 mole percent to about 30 mole percent, based on total amount of regeneration gas fed to the regenerator.

The burning of coke in the regeneration step is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated catalyst composition from the regeneration system and passing it through a catalyst cooler to form a cooled regenerated catalyst composition. The catalyst cooler, in an embodiment, is a heat exchanger that is located either internal or external to the regeneration system. Other methods for operating a regeneration system are in disclosed U.S. Pat. No. 6,290,916.

The regenerated catalyst composition withdrawn from the regeneration system, preferably from the catalyst cooler, is combined with a fresh molecular sieve catalyst composition and/or circulated molecular sieve catalyst composition and/or feedstock and/or fresh gas or liquids, and returned to the reactor(s). In a preferred embodiment, the regenerated catalyst is returned to the transition zone in the separation vessel. This allows the regenerated catalyst to be combined with the non-regenerated catalyst for even distribution between each of the multiple standpipe entry locations. In another embodiment, the regenerated catalyst composition withdrawn from the regeneration system is returned to the reactor(s) directly, preferably after passing through a catalyst cooler. A carrier, such as an inert gas, feedstock vapor, steam or the like, may be used, semi-continuously or continuously, to facilitate the introduction of the regenerated catalyst composition to the reactor system, preferably to the one or more reactor(s).

By controlling the flow of the regenerated catalyst composition or cooled regenerated catalyst composition from the regeneration system to the reactor system, the optimum level of coke on the molecular sieve catalyst composition entering the reactor is maintained. There are many techniques for controlling the flow of a catalyst composition described in Michael Louge, Experimental Techniques, Circulating Fluidized Beds, Grace, Avidan and Knowlton, eds., Blackie, pp. 336-337, 1997.

In various embodiments, for example, those involving the use of the present invention with a continuous regeneration system, the gas-displaced catalyst from the transition zone returned to the reaction zone can be at least 80%, or at least 85%, or at least 90%, or at least 92%, or at least 95 wt. % of that catalyst introduced to the transition zone. The catalyst is still very active, which is the surprising effect of the invention, so one benefits from retaining as much in the reaction and circulation zones as practical and, for example, only putting the minimal amount of catalyst to the regenerator needed to maintain a given average level of coke on catalyst in the reactor apparatus at the prevailing coke yield. In other embodiments, at least 80%, or at least 85%, or at least 90%, or at least 92%, or at least 95 wt. % of the catalyst introduced to the circulation zone is introduced to the transition zone.

Coke levels on the catalyst composition are measured by withdrawing the catalyst composition from the conversion process and determining its carbon content. Typical levels of coke on the molecular sieve catalyst composition, after regeneration, are in the range of from 0.01 weight percent to about 15 weight percent, such as from 0.1 weight percent to about 10 weight percent, for example, from about 0.2 weight percent to about 5 weight percent, and conveniently from about 0.3 weight percent to about 2 weight percent based on the weight of the molecular sieve.

The gaseous reactor effluent is typically withdrawn from the disengaging system and is passed through a recovery system. There are many well known recovery systems, techniques and sequences that are useful in separating olefin(s) and purifying olefin(s) from the gaseous effluent. Recovery systems generally comprise one or more or a combination of various separation, fractionation and/or distillation towers, columns, splitters, or trains, reaction systems such as ethylbenzene manufacture and other derivative processes such as aldehydes, ketones and ester manufacture, and other associated equipment, for example, various condensers, heat exchangers, refrigeration systems or chill trains, compressors, knock-out drums or pots, pumps, and the like.

Non-limiting examples of these towers, columns, splitters or trains used alone or in combination include one or more of a demethanizer, preferably a high temperature demethanizer, a deethanizer, a depropanizer, a wash tower often referred to as a caustic wash tower and/or quench tower, absorbers, adsorbers, membranes, ethylene (C2) splitter, propylene (C3) splitter and butene (C4) splitter.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in a preferred embodiment of the recovery system, the recovery system also includes a purification system. For example, the light olefin(s) produced particularly in a methanol to olefins (MTO) process are passed through a purification system that removes most or essentially all of the by-products or contaminants.

One skilled in the art will also appreciate that the light olefins produced by the oxygenate-to-olefin conversion reaction of the present invention, particularly the high purity olefins, can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305,538; 3,364,190; 5,892,079; 4,659,685; 4,076,698; 3,645,992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom, including high purity olefins. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

Typically, in converting one or more oxygenates to olefin(s) having 2 or 3 carbon atoms, a minor amount of hydrocarbons, particularly olefin(s), having 4 or more carbon atoms is also produced. The amount of $C_4+$ hydrocarbons is normally less than 20 weight percent, such as less than 10 weight percent, for example, less than 5 weight percent, and particularly less than 2 weight percent, based on the total weight of the effluent gas withdrawn from the process, excluding water. Typically, therefore the recovery system may include one or more reaction systems for converting the $C_4+$ impurities to useful products, for example, oligomerization to higher molecular weight olefins, optionally with subsequent saturation, or isomerization to desired isomers, or conversion to lower molecular weight olefins.

In another embodiment, this invention relates to:
1. a method for conducting an oxygenate conversion reaction comprising: providing an oxygenate feedstock, and a reactor apparatus that includes a reaction zone in fluid communication with a circulation zone, wherein the reaction zone has an inlet and an outlet, and the circulation zone has an inlet, an outlet and a transition zone, the transition zone including one or more displacing gas inlets; contacting the oxygenate feedstock with a catalytically effective amount of a gas-displaced catalyst in the reaction zone under oxygenate conversion conditions to form a product containing light olefins and an oxygenate-exposed catalyst, wherein the gas-displaced catalyst incorporates a silicoaluminophosphate molecular sieve with a $Si/Al_2$ ratio of at least 0.10 and no greater than 0.32, and the conditions include an oxygenate partial pressure in the reaction zone of at least 45 psi (310 kPa) and a reactor gas superficial velocity of at least 10 ft/s (3.0 m/s) at least one point in the reaction zone such that the oxygenate-exposed catalyst is conveyed through the reaction zone to the outlet of the reaction zone; providing at least a portion of the oxygenate-exposed catalyst from the outlet of the reaction zone to the inlet of the circulation zone, and passing the oxygenate-exposed catalyst through the transition zone while flowing a displacing gas from the one or more displacing gas inlets of the transition zone countercurrently through the oxygenate-exposed catalyst in the transition zone, the displacing gas having a superficial velocity of at least 0.1 ft/s (0.03 m/s) at least one point in the transition zone, to form the gas-displaced catalyst; providing at least a portion of the gas-displaced catalyst from the transition zone to the outlet of the circulation zone; and providing at least of portion of the gas-displaced catalyst from the outlet of the circulation zone to the inlet of the reaction zone to be at least a portion of catalyst for the contacting.
2. The method of paragraph 1 wherein the catalyst in the transition zone has a transition zone residence time and the catalyst within the reaction zone has a reaction zone residence time, and the transition zone residence time is at least two times that of the reaction zone residence time.
3. The method of paragraph 2 wherein the transition zone residence time is at least three times longer than the reaction zone residence time.
4. The method of any of paragraphs 1 to 3 wherein the $Si/Al_2$ ratio is at least 0.12 and no greater than 0.30.
5. The method of any of paragraphs 1 to 4 wherein the silicoaluminophosphate molecular sieve comprises SAPO-34, SAPO-18, or both.
6. The method of any of paragraphs 1 to 4 wherein the silicoaluminophosphate molecular sieve is selected from the group consisting of SAPO-34, SAPO-18, or a combination thereof.
7. The method of any of paragraphs 1 to 6 wherein the oxygenate partial pressure in the reaction zone is at least 50 psi (345 kPa).
8. The method of any of paragraphs 1 to 6 wherein the oxygenate partial pressure in the reaction zone is at least 45 psi (310 kPa) and no greater than 200 psi (1380 kPa).
9. The method of any of paragraphs 1 to 8 wherein at least one point in the reaction zone has a total pressure in the range about 45 psia (310 kPaa) to about 200 psia (1380 kPaa).
10. The method of any of paragraphs 1 to 9 wherein the gas superficial velocity is at least 20 ft/s near the inlet of the reaction zone.
11. The method of any of paragraphs 1 to 10 wherein the gas superficial velocity of the displacing gas is at least 0.16 ft/s (0.05 m/s) at least one point in the transition zone.
12. The method of any of paragraphs 1 to 10 wherein the gas superficial velocity of the displacing gas is at least 0.1 ft/s (0.03 m/s) at all points the transition zone.
13. The method of any of paragraphs 1 to 10 wherein the displacing gas superficial velocity at all points in the transition zone ranges from about 0.1 ft/s (0.03 m/s) to about 1.3 ft/s (0.40 m/s).
14. The method of any of paragraphs 1 to 13 further comprising conducting the light olefin product away from the reactor apparatus wherein no greater than 5% of the oxygenate-exposed catalyst flowing through the reactor outlet into the circulation zone are carried out of the reactor apparatus with the product including a light olefin.

15. The method of any of paragraphs 1 to 14 wherein at least 80 wt % of the catalyst from the inlet of the circulation zone is passed through the transition zone to the outlet of the circulation zone.
16. The method of any of paragraphs 1 to 15 wherein the conditions include an oxygenate conversion of at least 92 wt % as measured at the reactor outlet.
17. The method of any of paragraphs 1 to 16 wherein the conditions include weight hourly space velocity based on the silicoaluminophosphate molecular sieve of at least 25 hr$^{-1}$.
18. The method any of paragraphs 1 to 17 wherein the transition zone further comprises a plurality of baffle layers.
19. The method of paragraph 18 wherein an orientation of a first baffle layer is rotated by 90 degrees relative to an orientation of a second baffle layer.
20. The method of any of paragraphs 1 to 19 wherein the reactor apparatus comprises a plurality of reaction zones, and the circulation zone comprises a single transition zone and a further includes a plurality of standpipes equal in number to the reaction zones, with each standpipe having a discrete circulation zone outlet in fluid communication with a reaction zone inlet.
21. The method of any of paragraphs 1 to 19 wherein the reactor apparatus comprises a single reaction zone and the circulation zone comprises a single transition zone and no more than two standpipes in fluid communication with the reaction zone to return the catalyst to the single reaction zone.
22. The method of any of paragraphs 1 to 21 wherein at least one of the light olefins is polymerized to form a polymer product.

EXAMPLES

Example 1

A SAPO molecular sieve was prepared according to the method of Lok, U.S. Pat. No. 4,440,871, having a Si/Al$_2$ ratio of 0.30, and further having a cubic morphology of crystals approximately 1.5 to 2.0 microns per side. This SAPO molecular sieve was incorporated into an inactive alumina binder at a level of 40 wt % molecular sieve in the formulated catalyst, called Catalyst A.

Figure 9:
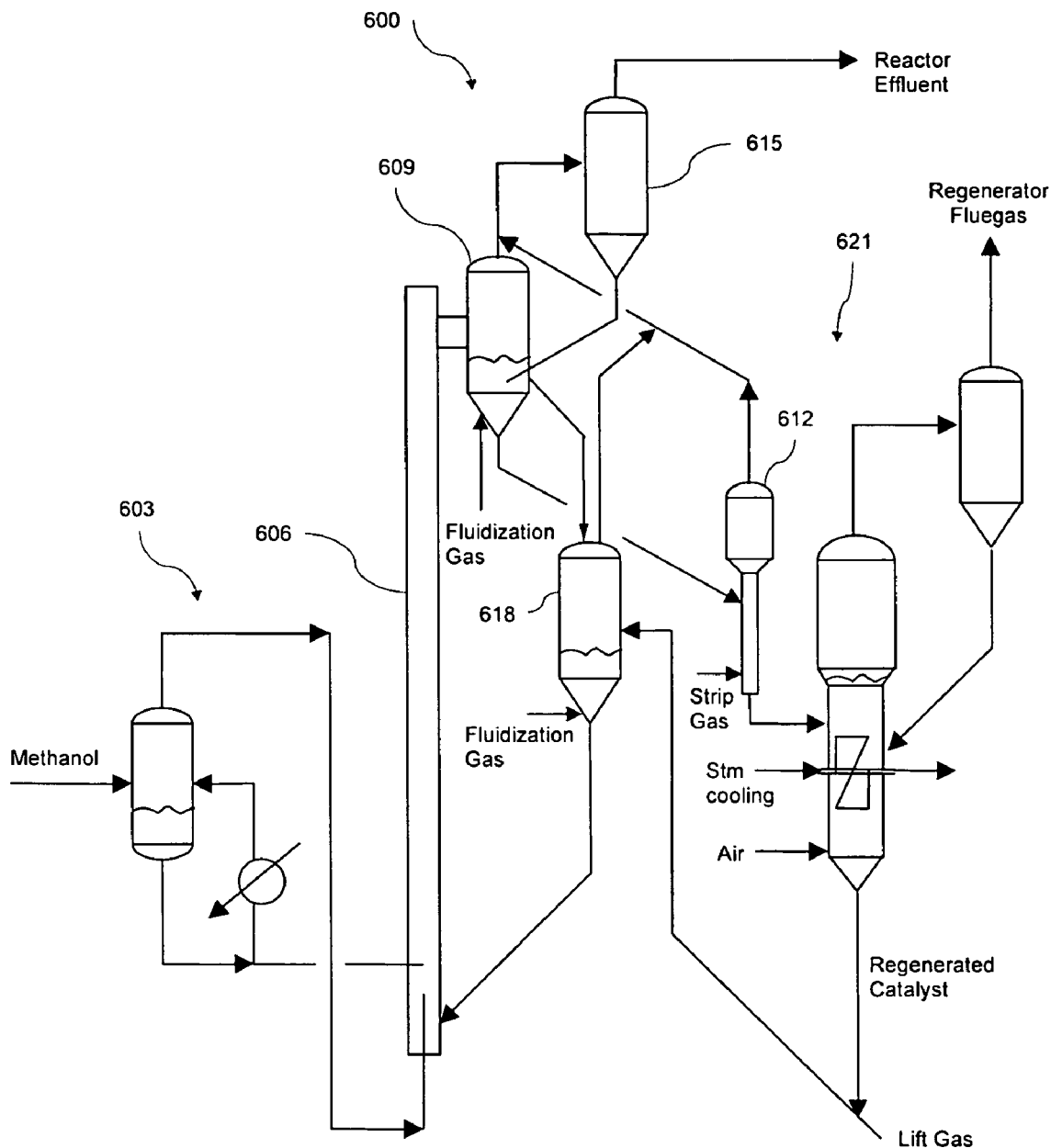
FIG. 9 schematically shows a large pilot plant reactor used in Examples 1-3.

A large pilot plant reactor with continuous regenerator 600, called Reactor/Regenerator A, as shown schematically in FIG. 9, was operated with Catalyst A. A feed vaporization system 603 received US Grade AA methanol and vaporized a portion thereof, providing both vapor and liquid feed to the reaction zone formed by cylindrical reactor vessel 606 at appropriate points as one element to control reaction zone temperature per the method of Kuechler, et. al., U.S. Pat. No. 6,555,240. Reactor 606 was 6 inches in inside diameter by about 100 feet tall, ending at the top in "blind T." Catalyst, product and unreacted feedstock flowing through reactor 606 emptied into first termination vessel 609. First termination vessel 609 was a cylinder comprising a right conical section at the bottom to collect separated catalyst. Very small volumes of fluidization gas, either nitrogen or steam, were added near the bottom of first termination vessel 609 to assist the flow of catalyst through the vessel into the associated catalyst transport conduits, and did not result in a countercurrent flow displacement gas to catalyst according to the method of the present invention. A small portion of the catalyst from first termination vessel 609 flowed through a conduit to continuous regenerator system 621, specifically to catalyst stripper 612, where the catalyst was stripped with a stripping gas. The stripping gas including hydrocarbons stripped from the catalyst exited the top of catalyst stripper 612 into a conduit to join the reaction product and unreacted oxygenate emanating from the top of first termination vessel 609 in another conduit. An inconsiderably small amount of catalyst entrained in the stripping gas from the catalyst stripper 612 may have been returned to the reactor apparatus.

The major portion of the catalyst from first termination vessel 609 flowed through a conduit to a second termination vessel 618 in which it was mixed with regenerated catalyst flowing in a conduit from the regenerator system 621. The mixture of circulated and regenerated catalyst flowed from the bottom of second termination vessel 618 through a conduit to the reactor 606 to contact the methanol feedstock at a point close to the introduction of the feedstock. Second termination vessel 618 was also a cylinder comprising a right conical section at the bottom to collect the catalyst. Very small volumes of fluidization gas, either nitrogen or steam, were added near the bottom of second termination vessel 618 to assist the flow of catalyst through the vessel into the associated catalyst transport conduit, and did not result in a countercurrent displacement of catalyst with displacement gas according to the method of the present invention. Released vapor reaction product entrained with the catalyst flowing into second termination vessel 618 exited the top of that vessel into a conduit to join the stripped gas and reaction product and unreacted oxygenate from catalyst stripper 612. The combined reaction product, unreacted oxygenate, released gas and stripping gas flowed into and out of a third termination vessel 615, containing a cyclone separator (not shown) interior to the vessel and not close coupled to the first termination vessel 609; any catalyst separated in third termination vessel 615 flowed through a conduit into first termination vessel 609, and there was no countercurrent displacement of the catalyst with a gas in third termination vessel 615.

About 100 kg of the formulated Catalyst A was placed in the reactor apparatus and operated in such a fashion that about 36 kg was in the reaction zone with the balance in the circulation zone. About 1000 lb/hr of US Grade AA methanol was fed to the reactor, the reaction zone was operated at an average temperature of about 450° C. (with a low of about 440° C. at the inlet and a high of about 460° C. at the outlet) and a total reactor pressure of about 40 psia a measured at the reactor inlet (near the introduction of oxygenate feedstock to the reactor 606), and olefins and unreacted oxygenate were produced as a vapor effluent. An appropriate amount of catalyst also resided in the regeneration system 621 to allow the entire system to function at a continuous, steady state in moving catalyst between the reactor apparatus 600 and the regeneration system 621, to maintain overall activity of the catalyst in the reactor apparatus 600, with withdrawal of coked catalyst from the reactor apparatus 600 to the regenerator system 621 being equal to return of regenerated catalyst from the regenerator system 621 to the reactor apparatus 600 to maintain the inventories noted above. Catalyst from the regenerator system 621 contained about 0.5 wt % carbonaceous material (coke) as measured with a standard LECO instrument. The concentration of all vapor components was measured at various locations in and around the reactor apparatus using gas chromatographic instruments, and yield of coke was measured by determining the rate of carbon and water production in the regenerator flue gas using appropriate on-line analytical techniques. This operation provided a roughly 98% conversion of methanol, with conversion in this instance determined as:

$$\frac{(\text{lb. CH}_2 \text{ in MeOH in feed}) - [(\text{lb. CH}_2 \text{ in MeOH} + DME \text{ in product})]}{(\text{lb. CH}_2 \text{ in MeOH in feed})}$$

where DME is dimethyl ether. By way of example, when feeding 100 lb/hr of pure methanol the MTO product contains 2.4 lbs of methanol and 1.6 lbs of DME, the "conversion" in this example would be derived as:

$$\frac{(100*14/32) - [(2.4*14/32) + (1.6*28/46)]}{(100*14/32)}$$

equaling 95.4%, where 14, 28, 32 and 46 are the molecular weights of methylene ($CH_2$) in methanol, methylene in DME, methanol per se and DME per se, respectively.

The pilot plant was thus operated according to the method of Lattner, et. al., U.S. Pat. No. 6,023,005, at the aforementioned conditions to provide in the reactor apparatus a formulated catalyst with a distribution of coke contents to increase olefin selectivity in the oxygenate conversion reaction. That is to say, any individual catalyst particle had a different level of coke according to the coke yield of the oxygenate conversion reaction and the actual residence time of that particular particle in the reaction zone prior to being withdrawn for regeneration. However, the average coke on catalyst of a relatively large sample of numerous particles was 7.1 wt. % and, that average remained stable at the given set of operating conditions.

Example 2

A portion of coked, formulated Catalyst A prepared in Example 1, having an average coke on catalyst of 7.1 wt. %, was taken from Reactor/Regenerator A and used in a series of laboratory experiments. A small sample of the catalyst was mixed with silicon carbide to provide heat inertia, and placed in a small bench scale, continuous, fixed bed reactor. The reactor was operated at given temperature, isothermally within about 10° C. from inlet to outlet, and at a given total reactor pressure. US Grade AA methanol was fed to the reactor at varying rates and times to provide a range of space times, and the products were analyzed with a gas chromatograph; thus, the oxygenate partial pressure in the reactor was about the same as the total reactor pressure (less the small proportion of water in the methanol). The reaction times prior to determining the product composition were short so as to put as little additional coke on the catalyst as practical during the course of the experiment, generally at or less than about an additional 0.1 wt. %, so as to not confound the data with changes in this parameter.

Figure 5:
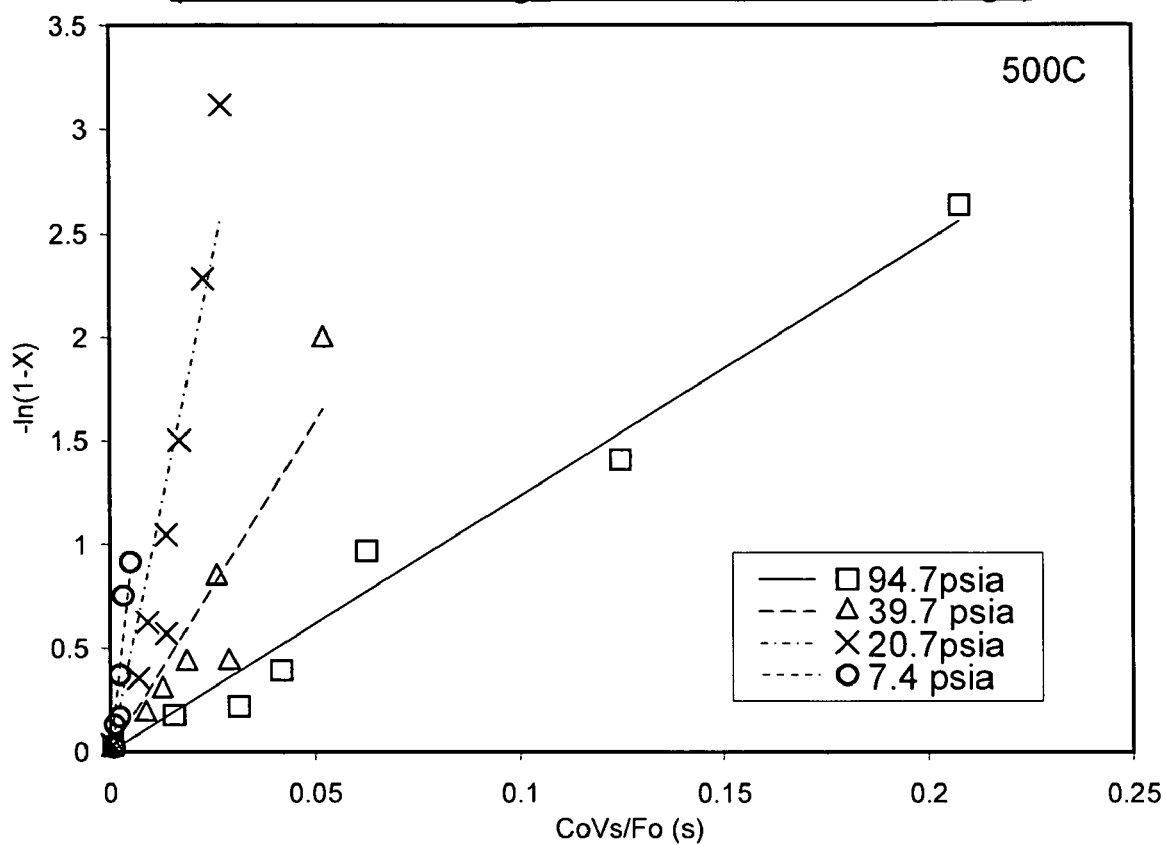
FIG. 5 is a pseudo first order plot of experiment results for a reaction system not of the method of the present invention.

The results of this series of experiments is plotted in FIG. 5 (all conducted at 500° C.), which represents what is called a "Pseudo First Order" plot (the term "pseudo" indicating one may not be absolutely, mechanistically certain the reaction system is totally first order kinetics, but it may behave that way well enough over a reasonable range of conditions of interest to make that a very useful approximation). In a Psuedo First Order plot, according to well known principles of chemical engineering, a first order kinetic expression for the disappearance of the reactant with time, k, is contemplated, having the form:

$$k=[-\ln(1-X)]/\tau \quad \text{(Eq. 1)}$$

where k is the first order rate constant in s−1, X is the fractional conversion of methanol according the definition of conversion defined in Example 1, and τ is the reaction space time, having units of seconds, is defined as:

$$\tau=[(Co)(Vs)]/Fo \quad \text{(Eq. 2)}$$

where Co is the initial methanol concentration in mol/liter, Vs is the volume of molecular sieve (not formulated catalyst) in liters, and Fo is the flowrate of methanol into the reactor in mol/second.

When one plots the results of $-\ln(1-X)$ against τ, as in FIG. 5, one can tell if the assumption of first order kinetics is reasonable if the data fall along a straight line, and if so, k is the value of the slope of the line. As seen in FIG. 5, at any given pressure, the data across a very wide range of conversions fall quite closely to a straight line, indicating that at any given pressure, the reaction behaves according to first order kinetics. However, note that the slope of each line decreases significantly with increasing pressure of methanol feed to the reactor. This demonstrates that under these continuous flow conditions, over a range of pressures, the apparent activity of the catalyst as represented by k decreases significantly with increasing pressure (thus, it is not a true first order reaction—if it were, k would not change with pressure). The decline is particularly steep at oxygenate partial pressures (in this case almost identical to the total pressure) exceeding about 40 psia.

Additional results, provided in Table 1, show that this decline in the apparent activity of SAPO catalysts for oxygenate conversion with increasing pressure under continuous flow conditions is consistent across several other key operating variables. Table 1 includes some of the data in FIG. 5; again, since we use very pure methanol, in all these data the methanol feed pressure is the essentially the same as the oxygenate partial pressure in the reactor.

TABLE 1

First order rate constant, k, for oxygenate conversion in a fixed bed, continuous feed flow unit

| Catalyst and Temperature | Methanol Feed Pressure (psia) | | | | |
|---|---|---|---|---|---|
| | 14.5 | 20.7 | 39.7 | 90.7 | 94.7 |
| A, 7.1 wt % average coke, 500° C. | 120 s$^{-1}$ | 94 s$^{-1}$ | 32 s$^{-1}$ | n/a | 12 s$^{-1}$ |
| A, fresh (no coke), 500° C. | 951 s$^{-1}$ | 850 s$^{-1}$ | 438 s$^{-1}$ | n/a | n/a |
| A, 7.1 wt % average coke, 400° C. | n/a | 25 s$^{-1}$ | n/a | 4 s$^{-1}$ | n/a |

Example 3

Reactor/Regenerator A was used in a series of experiments with the same catalyst and reactor operation described in Example 1. In these experiments, the reactor temperature was maintained at about 475° C. (with a low of about 465° C. at the inlet and a high of about 485° C. at the outlet), and the circulation rate back and forth between the reactor and regenerator was controlled such that the average coke on catalyst in the reactor was 7.0 wt %. The reactor pressure and WHSV were systematically changed, the composition of the reactor effluent exiting the reaction zone was analyzed (at the entrance to the first termination vessel 609), and the selectivity and conversion (according to Example 1) parameters noted. Also calculated according to Equation 1, above, was the apparent rate constant, k, for each run, based on the molecular sieve, not the formulated catalyst including binder. The results are provided in Table 2; the WHSV is based on the amount of formulated catalyst including binder.

TABLE 2

Fluidized bed pilot plant results with no appreciable inert stripping cycle

| Conditions | | Carbon Selectivity (wt %) | | | | | | | | Activity | |
| --- | --- | --- | --- | --- | --- | --- | --- | --- | --- | --- | --- |
| Pressure (psia) | WHSV $(hr^{-1})$ | C1 | C2$^-$ | C2$^o$ | C3$^-$ | C3$^o$ | C4's | C5's | Coke | Conversion Wt % | k $(s^{-1})$ |
| 32.2 | 27.9 | 1.2 | 37.3 | 0.6 | 39.7 | 1.7 | 10.9 | 4.6 | 4.0 | 92.4 | 66.0 |
| 32.2 | 22.8 | 1.2 | 37.5 | 0.6 | 39.6 | 1.7 | 10.9 | 4.7 | 3.8 | 95.3 | 63.9 |
| 32.2 | 14.9 | 1.2 | 37.4 | 0.8 | 38.8 | 1.8 | 11.0 | 5.1 | 3.9 | 97.8 | 52.4 |
| 39.7 | 32.0 | 1.2 | 36.9 | 0.6 | 40.4 | 1.7 | 11.2 | 4.1 | 3.9 | 90.6 | 56.6 |
| 39.7 | 23.0 | 1.2 | 37.0 | 0.6 | 40.0 | 1.7 | 11.2 | 4.7 | 3.6 | 95.7 | 54.0 |
| 39.7 | 17.3 | 1.2 | 37.0 | 0.8 | 39.5 | 1.9 | 11.1 | 4.7 | 3.8 | 98.0 | 50.4 |
| 64.7 | 30.9 | 1.3 | 34.1 | 0.8 | 40.8 | 2.4 | 12.1 | 4.5 | 4.0 | 95.7 | 45.0 |
| 64.7 | 19.9 | 1.2 | 34.1 | 0.9 | 40.7 | 2.4 | 12.0 | 4.8 | 3.9 | 98.6 | 39.0 |

Figure 10:
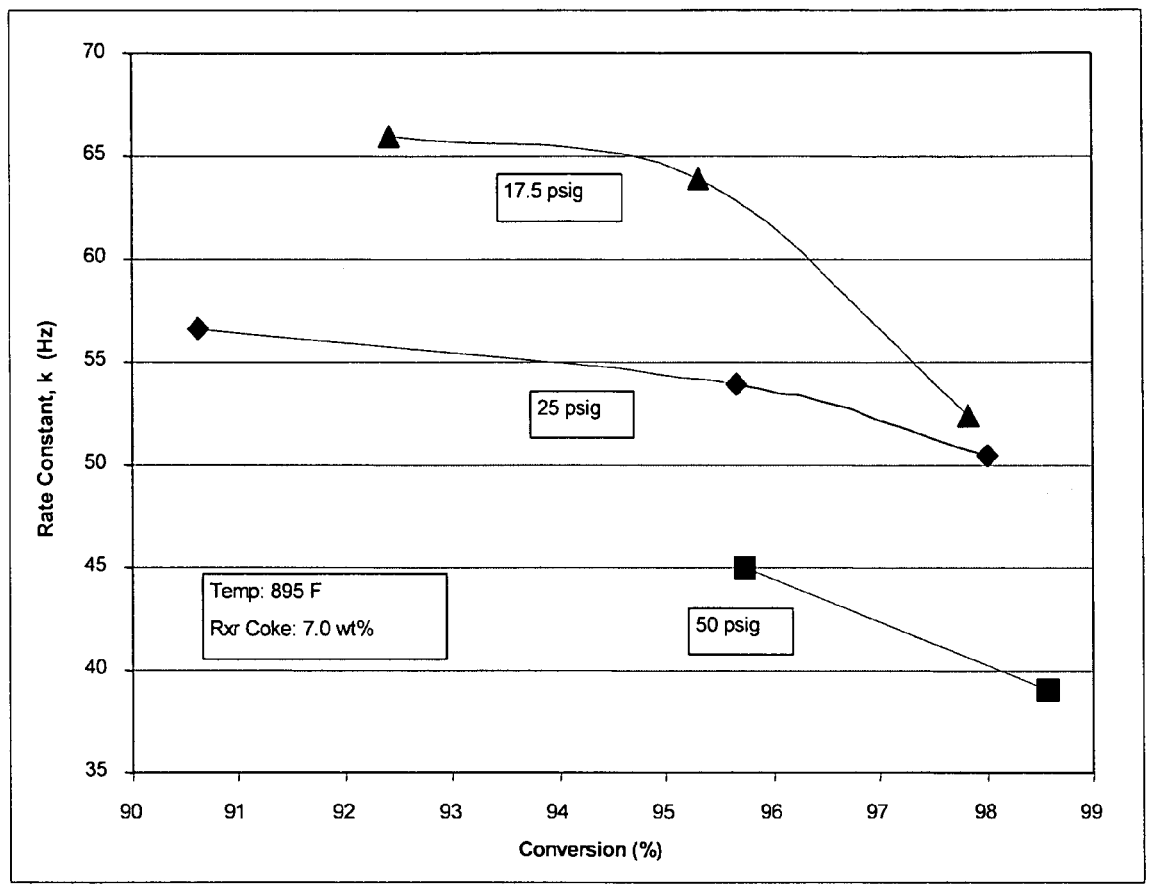
FIG. 10 plots catalyst activity as a function of reactor pressure and methanol conversion for a reaction system not of the method of the present invention.

Using the data in Table 2, the catalyst activity is plotted as a function of reactor pressure and methanol conversion in FIG. 10.

Note that even under fluidized bed conditions, without catalyst cycles of exposure to oxygenate and appreciable stripping according to the method of the present invention, a decline in apparent catalyst activity with increasing pressure is observed, just as was seen in Example 2 for fixed beds. Perhaps most peculiar is the decline in catalyst activity with increasing oxygenate conversion, particularly above about 94%, at any reactor pressure; methods to increase catalyst activity at these higher conversions would be of especial value.

Example 4

A SAPO molecular sieve was prepared according to the method of Janssen, et. al., U.S. Pat. No. 6,812,372, having a Si/Al$_2$ ratio of 0.19, and further having a rectangular parallelepiped morphology of crystals with dimensions of approximately 1.5×1.5×0.8 microns. This SAPO molecular sieve was incorporated into an inactive alumina binder at a level of 40 wt % molecular sieve in the formulated catalyst, called Catalyst B. This material was used to convert methanol to olefins in two experiments, identical in every respect except for introducing a catalyst feed exposure cycle in one, as discussed next.

A small sample of this fresh, uncoked catalyst was mixed with silicon carbide to provide heat inertia, and placed in a small bench scale, continuous, fixed bed reactor. The reactor was operated at given temperature, isothermally within about 10° C. from inlet to outlet, and at a given total reactor pressure. US Grade AA methanol was fed to the reactor at varying rates and times to provide a range of space times, and the products were analyzed with a gas chromatograph. In one experiment, methanol was converted across the catalyst continuously and in an uninterrupted fashion until the catalyst had converted the equivalent of about 12-13 grams of methanol per gram of contained molecular sieve in the catalyst (Cumulative grams Methanol Converted Per gram of molecular Sieve—CMCPS). In a second experiment, under otherwise identical conditions as those of the first, methanol was converted across the catalyst for three minutes of elapsed time, whereupon the catalyst was swept with pure steam for 10 minutes of elapsed time; this series of catalyst oxygenate exposures and inert sweeps (gas diplacements) was continued until the catalyst again had converted the equivalent of about 12-13 grams of methanol per gram of contained molecular sieve in the catalyst (for a total of three sweeps in this particular experiment). In both experiments, the methanol conversion conditions were a temperature of 475° C., a total reactor pressure of 70 psia and a WHSV based on the formulated catalyst of 100 hr$^{-1}$. The results are provided in FIGS. 6, 7 and 8.

Figure 6:
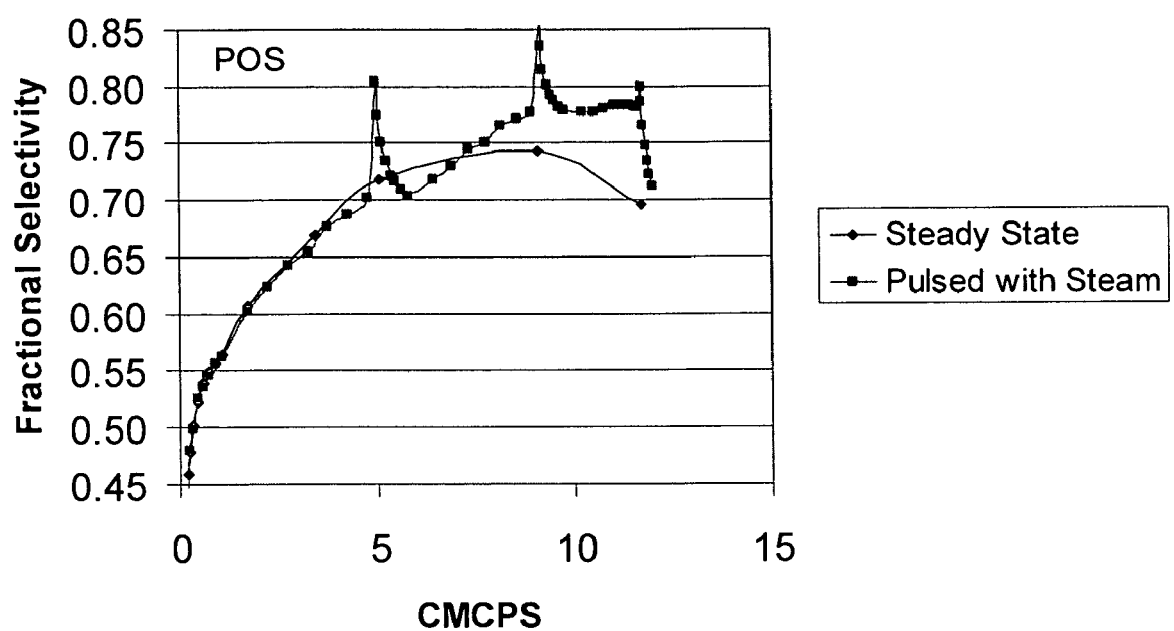
FIG. 6 plots the sum of the selectivities of ethylene and propylene, called Prime Olefin Selectivity or POS, vs. Cumulative grams Methanol Converted Per gram of molecular Sieve or CMCPS, for a reaction system directionally representing the method of the present invention.
Figure 7:
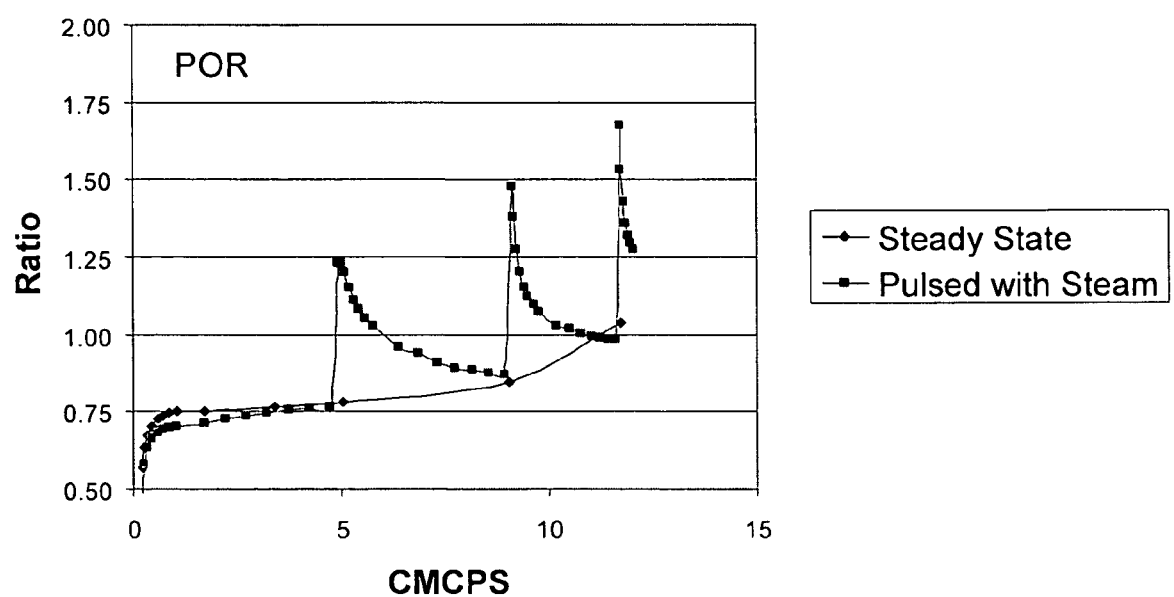
FIG. 7 plots the ratio of the selectivity of ethylene to that of propylene, called Prime Olefin Ratio or POR, vs. CMCPS, for a reaction system directionally representing the method of the present invention.
Figure 8:
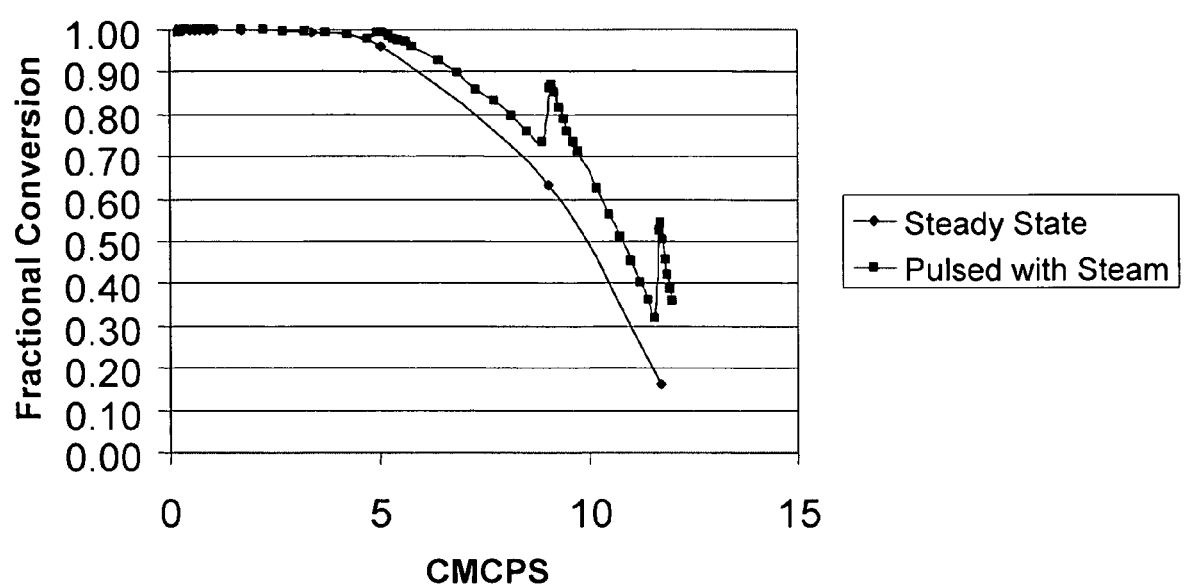
FIG. 8 plots the conversion of methanol according to the definition in Example 1, below, vs. CMCPS, for a reaction system directionally representing the method of the present invention.

FIG. 6 plots the sum of the fractional selectivities of ethylene and propylene, called Prime Olefin Selectivity or POS, vs. CMCPS. FIG. 7 plots the ratio of the selectivity of ethylene to that of propylene, called Prime Olefin Ratio or POR, vs. CMCPS. Prime Olefin Ratio as used herein is the quotient of the selectivity of ethylene divided by the selectivity of propylene. FIG. 8 plots the conversion of methanol according to the definition in Example 1 vs. CMCPS. Selectivities are on a carbon basis, that is, water has been taken out of the material balance and the hydrocarbon results normalized. Any material that may have been generated during the steam sweep was not analyzed.

Note the substantial increase in both POS and POR for the operation in which the modest activity SAPO catalysts at high pressures undergoes cycles of oxygenate exposure followed by inert gas displacement. It is clear that operating at relatively high pressures with catalysts of moderate Si/Al$_2$ ratio in a catalyst exposure cycle according to the present invention have unexpectedly different behavior than catalysts and conditions previously reported in the literature.

Example 5

Figure 11:
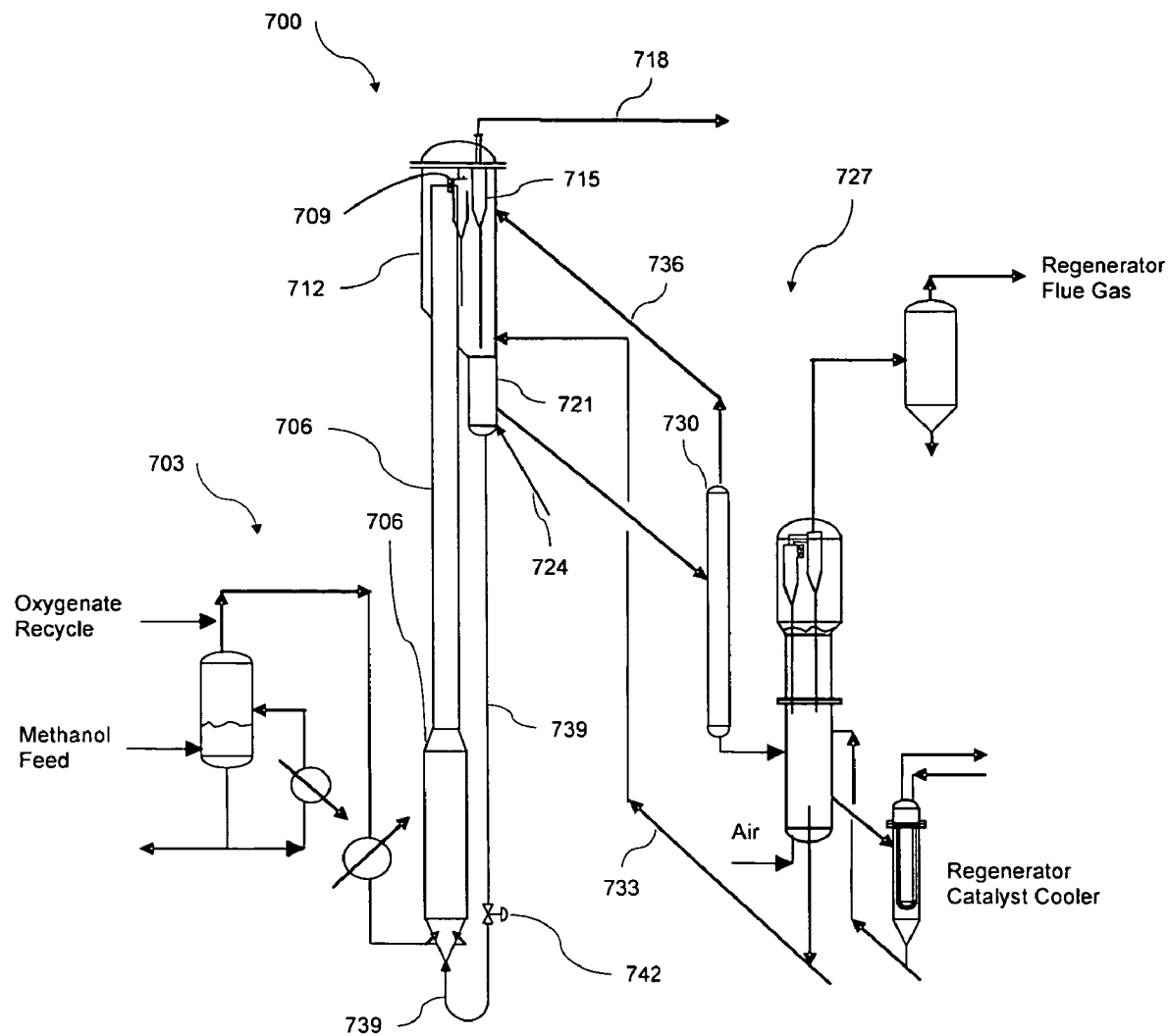
FIG. 11 shows a large pilot plant oxygenate conversion system of the method of the present invention used in Example 5.

Catalyst B of Example 4 was utilized in a series of experiments in a new, large pilot plant oxygenate conversion system 700 as shown in FIG. 11. A feed vaporization system 703 received approximately 2000 lb/hr of US Grade AA methanol and vaporized the entire flow except for a small liquid blowdown, providing only the vapor to the reaction zone formed by two stage frustum reactor vessel 706 near its bottom through several nozzles. Additional vapor recycle methanol and oxygenates, recovered in subsequent processing (not shown) of the reactor apparatus effluent was also introduced to feed vaporization system 703, comprising about 80 wt % methanol, 10 wt % water, 9 wt % C2+ oxygenates and 1 wt % hydrocarbons ranging from ethylene to xylene, and representing about 5 wt % of the entire oxygenate feedstock to reactor vessel 706.

Reactor vessel 706 had a bottom cylindrical section 8 inches in diameter by 18 feet tall, connected by a short, middle frusto-conical section with a 15 degree angle to a top cylindrical section 6 inches in diameter by 92 feet tall, in a configuration as disclosed in the method of Smith, et. al., U.S. Patent Application 20040024276. The total vaporized feedstock entering reaction vessel 706 was joined with circulated, gas-displaced catalyst and some regenerated catalyst. Catalyst, product, unreacted feedstock and minor amounts of steam flowed up through the reaction zone defined by reactor vessel 706 into a primary close coupled cyclone 709 contained within termination vessel 712. Separated catalyst, now oxygenate exposed, flowed down through a dipleg of primary close coupled cyclone 709 while product, unreacted feedstock and steam, along with a small amount of entrained catalyst, flowed out the top of cyclone 709 into openly close coupled secondary cyclone 715. Further separation of oxygenate-exposed catalyst and vapor occurred in openly close coupled secondary cyclone 715, also contained within termination vessel 712. The ultimate reaction products and any unconverted feedstock and diluent (steam), including any such materials from within the termination vessel 716, exited the top of openly close coupled secondary cyclone 715 and flowed out of the reactor apparatus through line 718, and additional separated catalyst flowed down through the dipleg of openly close coupled secondary cyclone 715. An extremely small amount of catalyst was entrained with the vapor material exiting the reactor apparatus in line 718.

Termination vessel 712 comprised a central cylinder with an elliptical top head and an angled frusto-conical bottom section, the bottom circular section of which joined the top of right cylindrical transition zone 721. Also entering termination vessel 712 was regenerated catalyst, containing about 0.5 wt % coke on catalyst as measured with a standard LECO instrument, from continuous regeneration system 727 (fitted with a catalyst cooler) via a conduit 733. Further, stripping gas and stripped hydrocarbons from the top of regeneration catalyst stripper 730 entered termination vessel 712 via conduit 736. An inconsiderably small amount of catalyst entrained in the stripping gas from the regeneration catalyst stripper 730 may have entered termination vessel 712.

Catalyst from the diplegs of the cyclones 709 and 715 fell down through termination vessel 712, along with the regenerated catalyst, and into the top of transition zone 721, carrying with it some product and unreacted oxygenated that was also present in the diplegs and was otherwise present in the termination vessel 712. Displacing steam through a line 724 entered the bottom of transition zone 721, appropriately distributed in volumes as disclosed herein within transition zone 721 to have good countercurrent contacting with the catalyst entering the top of transition zone 721, and further to provide an appropriate defluidization zone below the points/sections where the displacing steam was introduced. No contacting internals were present in transition zone 721. A small portion of gas-displaced catalyst was withdrawn from transition zone 721 to continuous regeneration system 727, specifically to regeneration catalyst stripper 730. The amount of catalyst moving continuously between the reactor apparatus 700 and the continuous regeneration system 727 was maintained in accordance with the coke yield of the oxygenate conversion reaction to maintain a desired average coke on catalyst in the reactor apparatus according to the method of Lattner, U.S. Pat. No. 6,023,005.

The major portion of the catalyst from transition zone 721, now properly gas-displaced, flowed into the top of standpipe 739. The rate of catalyst circulation in the reactor apparatus, and further the amount of catalyst within the circulation zone (primarily as catalyst inventory within the transition zone) and in the reaction zone was controlled with a slide valve 742 to control the rate of catalyst flow through standpipe 739. Regenerated and circulated gas-displaced catalyst exited the circulation zone at the bottom end of standpipe 739 into the reaction zone formed by reactor vessel 706 to contact the feedstock.

With a constant flow of catalyst back and forth between the reactor apparatus and the regeneration system, providing higher resistance to catalyst flow through slide valve 742 would cause more catalyst to stack up in the circulation zone, and further cause essentially the same amount of catalyst to be taken from the reaction zone. This action would also reduce the rate of catalyst circulated to the reaction zone; at a constant feedstock rate to the reactor apparatus this would reduce what is called the Catalyst to Oil ratio, or Cat/Oil, or C/O to the reaction zone (borrowing a term from Cat Cracking art). Providing lower resistance to catalyst flow through slide valve 742 would cause the exact converse result.

While maintaining a constant inventory of about 200 kg catalyst in the reaction zone and circulation zone, a constant oxygenate feedstock rate and a constant flow of catalyst back and forth between the reactor apparatus and the regeneration system, the operating pressure of the reactor apparatus and a number of other parameters was systematically varied. The composition of all vapor components was measured at various locations around the reactor apparatus using on-line gas chromatograph instruments, and yield of coke was measured by determining the rate of carbon and water production in the regenerator flue gas using appropriate on-line analytical techniques. Key results are shown in FIGS. 12, 13, 14, 15, 16, 17 and 18. For FIGS. 12-16, vapor compositions used in developing the information is for the entire reactor apparatus effluent in line 718. For FIGS. 17-18, the vapor compositions were determined at the outlet of the reaction zone just prior to entering primary close coupled cyclone 709 (labeled "GC-1 on the figures). All selectivity results for all these figures are on a carbon basis, as discussed above. The data points on all these figures are the mathematical average of numerous data values taken over significant periods of time at steady state operation, and the bars around the data points for all these figures are statistical error bars representing 2 sigma, calculated according to standard statistical procedures.

FIG. 12 demonstrates the remarkable result that, using the method of the present invention to properly gas displace the circulating catalyst, the decline in catalyst activity observed without using the present invention can not only be mitigated, but even reversed; the catalyst activity, k, determined by Equation 1 above, actually increases with increasing pressure. A very substantial benefit of this is a significantly reduced cat/oil ratio to achieve a given conversion, as demonstrated in FIG. 13 reflecting the same operating states provided in FIG. 12, and additionally showing the impact of varying levels of coke on catalyst. As noted above, the changing cat/oil ratio results in changing amounts of catalyst within the circulation and reaction zones, and the WHSV based on the formulated Catalyst B at the conditions shown in FIG. 12 is provided in Table 3. The WHSV is increasing in response to an increase in methanol partial pressure as disclosed in Fung, et. al., U.S. Pat. No. 6,768,034.

TABLE 3

Reactor WHSV (Formulated Catalyst B) Corresponding To Catalyst Activities In FIG. 12

| | | | |
|---|---|---|---|
| Pressure (psig) | 25.2 | 40.1 | 53.1 |
| K (s$^{-1}$) | 95.0 | 115.1 | 136.6 |
| WHSV (hr$^{-1}$) | 47.4 | 78.4 | 112.3 |
| Conversion, % | 94.8 | 95.0 | 95.3 |
| Ratio of Residence Times of Catalyst in Transition Zone to Catalyst in Reaction Zone | 2.0 | 3.5 | 5.5 |

It must also be noted that during these experiments, in the course of going from 25 to 53 psig, the amount of catalyst in the reaction zone decreased by a factor of about 2.4, with that inventory being redirected to the circulation zone, the large majority of which is retained in the transition zone. At steady state in a continuous operation of moving catalyst between the reaction and circulation zones, the residence time of catalyst in each zone is about equal to the mass of catalyst in each zone, and the ratio of residence times is also provided in Table 3.

As evidenced by FIG. 14, again, the results of the method of the present invention are distinctly different from the method of Vaughn, et. al., U.S. Pat. No. 6,613,950, which teaches that coke yield should decrease significantly (catalyst activity should be maintained for a much longer period of time) in an oxygenate conversion reaction with an intermittent hydrocarbon stripping of the catalyst.

Another remarkable feature of the method of the present invention is that despite the large increase in the ratio of the residence time of catalyst in the transition zone to the residence time of catalyst in the reaction zone, the selectivity to desired products in the overall product from the reaction apparatus does not change appreciably, as shown in FIGS. 15 and 16. This is distinctly different from the results that would be expected from the method of Coute', et. al., U.S. Pat. No. 6,673,978, which teaches that such a significant change in this ratio would substantially reduce desired product selectivity and substantially increase undesirable byproduct selectivity, especially methane and propane.

FIGS. 17 and 18 also show how, within the method of the present invention, POS and POR at any operating pressure may be adjusted by changing the average coke on catalyst within the reactor apparatus in accordance with the operation of a continuous regeneration system.

What is claimed is:

1. A method for conducting an oxygenate conversion reaction comprising:
    providing an oxygenate feedstock, and a reactor apparatus that includes a reaction zone in fluid communication with a circulation zone, wherein said reaction zone has an inlet and an outlet, and said circulation zone has an inlet, an outlet and a transition zone, said transition zone including one or more displacing gas inlets;
    contacting the oxygenate feedstock with a catalytically effective amount of a gas-displaced catalyst in the reaction zone under oxygenate conversion conditions to form a product containing light olefins and an oxygenate-exposed catalyst, wherein the gas-displaced catalyst incorporates a silicoaluminophosphate molecular sieve with a Si/Al$_2$ ratio of at least 0.10 and no greater than 0.32, and the conditions include an oxygenate partial pressure in the reaction zone of at least 45 psi (310 kPa) and a reactor gas superficial velocity of at least 10 ft/s (3.0 m/s) at at least one point in the reaction zone such that the oxygenate-exposed catalyst is conveyed through the reaction zone to the outlet of the reaction zone;
    providing at least a portion of the oxygenate-exposed catalyst from the outlet of the reaction zone to the inlet of the circulation zone, and passing the oxygenate-exposed catalyst through the transition zone while flowing a displacing gas from the one or more displacing gas inlets of the transition zone countercurrently through the oxygenate-exposed catalyst in the transition zone, the displacing gas having a superficial velocity ranges from about 0.1 ft/s (0.03 m/s) to about 1.3 ft/s (0.40 m/s) at at least one point in the transition zone, to form the gas-displaced catalyst;
    providing at least a portion of the gas-displaced catalyst from the transition zone to the outlet of the circulation zone; and
    providing at least of portion of the gas-displaced catalyst from the outlet of the circulation zone to the inlet of the reaction zone to be at least a portion of catalyst for the contacting.

2. The method of claim 1 wherein the catalyst in the transition zone has a transition zone residence time and the catalyst within the reaction zone has a reaction zone residence time, and the transition zone residence time is at least two times that of the reaction zone residence time.

3. The method of claim 2 wherein the transition zone residence time is at least three times longer than the reaction zone residence time.

4. The method of claim 1 wherein the Si/Al$_2$ ratio is at least 0.12 and no greater than 0.30.

5. The method of claim 1 wherein the silicoaluminophosphate molecular sieve comprises SAPO-34, SAPO-18, or both.

6. The method of claim 1 wherein the silicoaluminophosphate molecular sieve is selected from the group consisting of SAPO-34, SAPO-18, or a combination thereof.

7. The method of claim 1 wherein the oxygenate partial pressure in the reaction zone is at least 50 psia (345 kPaa).

8. The method of claim 1 wherein the oxygenate partial pressure in the reaction zone is at least 45 psia (310 kPaa) and not greater than 200 psia (1380 kPaa).

9. The method of claim 1 wherein at least one point in the reaction zone has a total pressure in the range about 45 psia (310 kPaa) to about 200 psia (1380kPaa).

10. The method of claim 1 wherein the reactor gas superficial velocity is at least 20 ft/s (6.1 m/s) at at least one point in the reaction zone.

11. The method of claim 1 wherein the displacing gas superficial velocity is at least 0.16 ft/s (0.05 m/s) at at least one point in the transition zone.

12. The method of claim 1 wherein the displacing gas superficial velocity ranges from about 0.1 ft/s (0.03 m/s) to about 1.3 ft/s (0.40 m/s) at all points in the transition zone.

13. The method of claim 1 further comprising conducting the light olefin product away from the reactor apparatus wherein no greater than 5% of the oxygenate-exposed catalyst flowing through the reactor outlet into the circulation zone are carried out of the reactor apparatus with the product including a light olefin.

14. The method of claim 1 wherein at least 80 wt% of the catalyst from the inlet of the circulation zone is passed through the transition zone to the outlet of the circulation zone.

15. The method of claim 1 wherein the conditions include an oxygenate conversion of at least 92 wt % as measured at the reactor outlet.

16. The method of claim 1 wherein the conditions include weight hourly space velocity based on the silicoaluminophosphate molecular sieve of at least 25 hr$^{-1}$.

17. The method of claim 1 wherein the transition zone further comprises a plurality of baffle layers.

18. The method of claim 17 wherein an orientation of a first baffle layer is rotated by 90 degrees relative to an orientation of a second baffle layer.

19. The method of claim 1 wherein the reactor apparatus comprises a plurality of reaction zones, and the circulation zone comprises a single transition zone and further includes a plurality of standpipes equal in number to the reaction zones, with each standpipe having a discrete circulation zone outlet in fluid communication with a reaction zone inlet.

20. The method of claim 1 wherein the reactor apparatus comprises a single reaction zone, and the circulation zone comprises a single transition zone and no more than two standpipes in fluid communication with the single reaction zone to return the catalyst to the single reaction zone.

21. The method of claim 1 wherein at least one of said light olefins is polymerized to form a polymer product.

* * * * *